US008563051B2

(12) United States Patent
Samuel et al.

(10) Patent No.: US 8,563,051 B2
(45) Date of Patent: *Oct. 22, 2013

(54) HERBAL COMPOSITION FOR WEIGHT MANAGEMENT

(75) Inventors: Philip Samuel, Bangalore (IN); Fred Pescatore, New York, NY (US)

(73) Assignee: InQpharm Sdn Bhd, Kuala Lumpur (MY)

( * ) Notice: Subject to any disclaimer, the term of this patent is extended or adjusted under 35 U.S.C. 154(b) by 0 days.

This patent is subject to a terminal disclaimer.

(21) Appl. No.: 13/336,732

(22) Filed: Dec. 23, 2011

(65) Prior Publication Data

US 2012/0164264 A1    Jun. 28, 2012

Related U.S. Application Data

(63) Continuation of application No. 12/092,161, filed as application No. PCT/US2006/042943 on Nov. 3, 2006, now Pat. No. 8,097,286.

(60) Provisional application No. 60/733,924, filed on Nov. 4, 2005.

(51) Int. Cl.
*A61K 31/194* (2006.01)
*A61K 31/437* (2006.01)
*A61K 36/82* (2006.01)
*A61K 65/00* (2006.01)

(52) U.S. Cl.
USPC ........... 424/725; 424/729; 514/229; 514/574; 514/909

(58) Field of Classification Search
None
See application file for complete search history.

(56) References Cited

U.S. PATENT DOCUMENTS

| | | | |
|---|---|---|---|
| 3,764,692 | A | 10/1973 | Lowenstein |
| 6,399,089 | B1 | 6/2002 | Yegorova et al. |
| 6,784,206 | B2 | 8/2004 | Udell et al. |
| 6,830,765 | B2 | 12/2004 | Rombi |
| 2004/0166181 | A1 | 8/2004 | Hegenauer et al. |
| 2004/0186181 | A1 | 9/2004 | Bagchi et al. |
| 2004/0259937 | A1 | 12/2004 | Samuel et al. |
| 2005/0003026 | A1 | 1/2005 | Bok et al. |
| 2005/0003068 | A1 | 1/2005 | Kester et al. |
| 2005/0181044 | A1 | 8/2005 | Romero |
| 2006/0051435 | A1 | 3/2006 | Udell et al. |
| 2008/0268075 | A1 | 10/2008 | Samuel et al. |

FOREIGN PATENT DOCUMENTS

| | | | |
|---|---|---|---|
| EP | 0 739 629 | A1 | 10/1996 |
| FR | 2 865 402 | A1 | 7/2005 |
| JP | 04345693 | A | 12/1992 |
| JP | 2002308766 | A | 10/2002 |
| WO | WO 2005/014020 | | 2/2005 |
| WO | WO 2005/032570 | | 4/2005 |
| WO | WO 2005/067952 | | 7/2005 |

OTHER PUBLICATIONS

Arion et al., "Chlorogenic acid analogue S3483 a potent competitive inhibitor of the hepatic and renal glucose-6-phosphate systems," Arch Biochem Biophys. vol. 351, No. 2, (1998) , pp. 279-285.
Hayamizu et al., "Effects of Garcinia cambogia (Hydroxycitric acid) on Visceral fat accumulation. A double-blind, randomized, placebo-controlled trial," Current Therapeutic Research, vol. 64 , No. 8 (2003), pp. 551-556.
Hemmerle et al., "Chlorogenic acid and synthetic chlorogenic acid derivatives: novel inhibitors of hepatic glucose-6-phosphate translocase," J Med Chem, vol. 40, No. 2, (1997), pp. 137-145.
Hertog et al., "Flavonoid intake and long-term risk of coronary heart disease and cancer in the Seven Countries Study," Arch Intern Med., vol. 155, No. 4 (1995) pp. 381-386.
Heymsfield et al., "Garcinia cambogia (Hydroxycitric acid) as a potential antiobesity agent: A randomized controlled trial," JAMA, vol. 280, No. 18 (1998) pp. 1596-1600.
Hollamn et al., "Tea flavonols in cardiovascular disease and cancer epidemiology," Proc Soc Exp Biol Med., vol. 220 (1999) 198-202.
Ikeda et al., "Effectiveness and safety of Banabamin tablet containing an extract from banaba in patients with mild type 2 diabetes," Japan Pharmacol Ther., vol. 27, No. 5, (1999), pp. 67-73 (Abstract).
Johnston et al., "Coffee acutely modifies gastrointestianal hormone secretion and glucose tolerance in humans: glycemic effects of chlorogenic acid caffeine," Am J Clin Nutr., vol. 78, No. 4, (2003), pp. 728-733.
Juneja et al., "L-theanine—a unique amino acid of green tea and its relaxation effect in humans," Trends Food Sci Tech, vol. 10 (1999) pp. 199-204.
Knowler et al., "Reduction in the incidence of type 2 diabetes with lifestyle intervention or Metformin," N. Engl J Med., vol. 346, No. 6 (2002), pp. 393-403.
Loe et al., "Gas chromatography/mass spectrometry method to quantify blood hydroxycitrate concentration," Anal Biochem., vol. 292, No. 1 (2001), pp. 148-154.
Loe et al., "Time course of hydroxycitrate clearance in fasting and fed humans," FASEB, vol. 15, No. 4 (2001), A632 (Abs. 501.1).
Mahendran et al., "The modulating effect of Garcinia cambogia extract on ethanol induced peroidative damage in rats," Indian J of Pharmacology, vol. 33 (2001), pp. 87-91.
Mason, "200 mg of Zen: L-theanine boosts alpha waves, promotes alert relaxation," Alternative & Complementary Therapies, vol. 7 (2001), pp. 91-99.
Murakami et al., "Screening of plant constituents for effect on glucose transport activity in Ehrlich ascites tumor cells," Chem and Pharm Bulletin, vol. 41, No. 12 (1993), pp. 2129-2131.
Nathan, "Long-term complications of diabetes mellitus," N Eng J Med., vol. 323, No. 23 (1993), pp. 1676-1685.

(Continued)

*Primary Examiner* — Michele C. Flood
(74) *Attorney, Agent, or Firm* — Pauley Petersen & Erickson

(57) ABSTRACT

Herbal extracts composition suitable for weight management in mammals is disclosed. The composition comprises a mixture of *Garcinia* extract, Green tea extract, Green coffee extract and Banaba extract. The method of reducing weight, and treating diabetes in mammals involve oral administration of the composition. The invention further relates to a method of producing and standardizing the individual extract useful for human health.

44 Claims, 5 Drawing Sheets

(56) References Cited

OTHER PUBLICATIONS

"Detection, Evaluation, and Treatment of High Blood Cholesterol in Adults (Adult Treatment Panel III)," NIH, Publication No. 02-5215 (2002).

Preuss et al., "Effect of hydroxycitric acid on weight loss, body mass index and plasma leptin levels in human subjects," FASEB J., vol. 16, No. 5 (2002), A1020.

Preuss et al., "Efficacy of a novel, natural extract of (-)-hydroxycitric adcid (HCA-SX) and a combination of HCA-SX, niacin-bound chromium and Gymnema sylvestre extract in weight management in human volunteers . A pilot study," Nutritional Research, vol. 24 (2004), pp. 45-58.

Schaefer, "Coffee consumption and type 2 diabetes mellitus," Ann Intern Med., vol. 141 (2004) p. 321.

Shirai et al., "Single forced oral administration toxicity test on mouse by banaba extract," Jpn Pharmacol Ther., vol. 22, No. 11 (1994) pp. 119-121 (Abstract).

Sullivan et al., "Metabolic regulation as a control for lipid disorders. I. influence of (-)-hydroxycitrate on experimentally induced obesity in the rodent," Am J Clin Nutr., vol. 30 (1977), pp. 767-776.

Suzuki et al., "Antiobesity activity of extracts from Lagerstroemia speciosa L. leaves on female KK-AY mice," J. Nutr Sci Vitaminol, vol. 45, No. 6 (1999), pp. 791-795.

Tommasi et al., "Hypoglycemic effects of sensquiterpene glycosides and polyhydroxylated triterpenoids of eriobotrya japonica," Planta Med., vol. 57 (1991), pp. 414-416.

Tuomilehto et al., "Prevention of type 2 diabetes mellitus by changes in lifestyle among subjects with impaired glucose tolerance," N Engl J Med., vol. 344, No. 18, (2001), pp. 1343-1350

Van Dam et al., "Coffee composition and risk of type 2 diabetes a systematic reveiw, " J Am Med Assoc., vol. 294, No. 1, (2005), pp. 97-104.

Van Loon et al., "Effects of acute (-)-hydroxycitrate supplementation on substrate metabolism at rest and during exercise in humans," Am J Clin Nutr., vol. 72, No. 6 (2000), pp. 1445-1450.

Weisburger, "Tea and health: the underlying mechanisms," Proc Soc Exp Biol Med., vol. 220, (1999), pp. 271-275.

Wild et al., "Global prevalence of diabetes: Estimates for the year 2000 and projections for 2030," Diabetes Care, vol. 27, No. 5, (2004), pp. 1047-1053.

Udell, R.G., et al. "Nutritional Supplement for Body Fat Reduction," U.S. Appl. No. 60/602,921, filed Aug. 19, 2004 (41 pages).

HERBAL COMPOSITION FOR WEIGHT MANAGEMENT

CROSS REFERENCE TO RELATED APPLICATION

This application is a continuation of U.S. Patent Application, Ser. No. 12/092,161, filed on 10 Jun. 2008, which is a National Phase entry of PCT/US2006/042943, filed on 3 Nov. 2006, which claims priority to, and the benefit of, U.S. Provisional Patent Application Ser. No. 60/733,924, filed on 4 Nov. 2005. The co-pending parent application is hereby incorporated by reference herein in its entirety and is made a part hereof, including but not limited to those portions which specifically appear hereinafter.

BACKGROUND OF THE INVENTION

Obesity and overweight are risk factors for type 2 diabetes, hypertension and coronary heart disease that cause morbidity, mortality and high health-care expenditure.

Obesity is the number one nutritional problem in the U.S. An estimated one third of Americans are overweight, with an additional 25 percent being classified as obese. Being overweight significantly increases a person's risk of developing diabetes, heart disease, stroke, and other diseases. The clustering of hyperinsulinemia, dyslipidemia, type 2 diabetes mellitus and hyper tension is called insulin resistance syndrome or metabolic syndrome, and syndrome X. Accordingly, evaluation of obesity for the prevention of syndrome X must be conducted using not only body weight or Body Mass Index (BMI) but also Visceral Fat Accumulation (VFA) [Hayamizu et al. 2003].

Type 2 diabetes is a chronic disease associated with high rates of morbidity and premature mortality [Nathan et al. 1993]. An alarming increase in the prevalence of type 2 diabetes is expected [Wild et al. 2004] and the need for preventive action is widely acknowledged. While increased physical activity and restriction of energy intake can substantially reduce the incidence of type 2 diabetes [Tuomilehto et al. 2001; Knowler et al. 2002] insight into the role of other lifestyle factors may contribute to additional prevention strategies for type 2 diabetes.

The objective of the present invention is to provide a simultaneous multi approach way to control weight gain by providing a herbal extracts composition which can increase metabolism, thermogenesis, and control diabetes mellitus. Furthermore, it has been established that full spectrum herbal extract has more biological activity than the purified herbal extracts which is devoid of other important micronutrient essential for synergistic effect. As a result the present invention strives to give each component of the herbal extracts composition as a full spectrum extract containing all the biologically active compounds present in the herb.

SUMMARY OF THE INVENTION

The present invention provides a means for weight management in the form of a herbal composition comprising *Garcinia cambogia* extract, Green tea extract, Green coffee extract and Banaba extract. This composition can be made easily for human consumption to give desired weight loss. The reduction in weight can be achieved through normalized blood sugar levels, decreased fat synthesis, enhanced metabolism, lowering the risk of type 2 diabetes mellitus and anti-hypertension.

DETAILED DESCRIPTION

Figure 1:
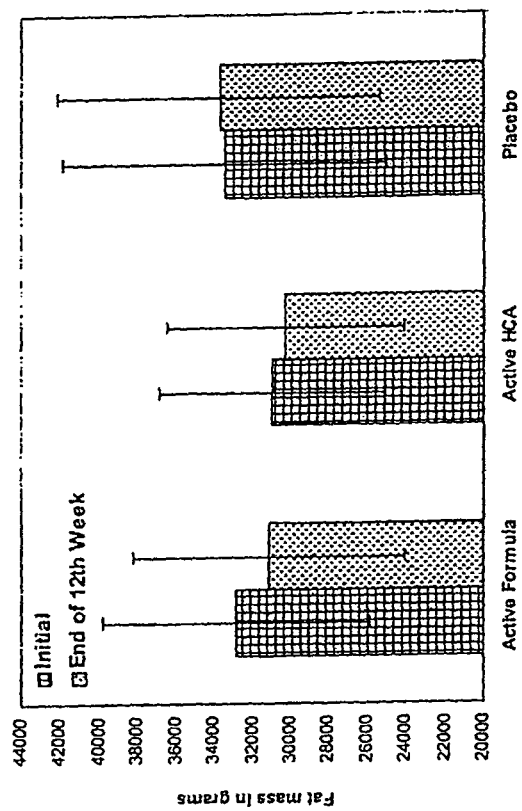
FIG. 1. is a graphical representation of the change in mean fat mass between baseline and end of study for all three groups.

Various embodiments of the present invention will be described in detail with reference to the tables and figures, wherein like reference numerals represent like parts throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

The invention relates to herbal extracts composition for weight management and treating diabetes in humans. The invention further relates to a method for producing and standardizing the herbal extracts composition useful for human health.

The herbal composition of the present invention comprises *Garcinia* extract, Green tea extract, Green coffee extract and Banaba extract. The four extracts are known for their weight control and, or other health benefits by different mechanisms but individually none provide all the desired weight control and health benefits. Indeed there arise a need to provide an improved composition for weight control and other preferred health benefits. The purpose of the present invention is to get all the desired benefits using a single herbal composition comprising *Garcinia cambogia* extract, Green tea extract, Green coffee extract and Banaba extract.

1. *Garcinia Cambogla*

*Garcinia Cambogla* is an exotic fruit grown in South India and has been used for centuries to impart a distinctive sour flavor to Indian cooking. The active ingredient extracted from the *Garcinia Cambogia* (Indica) is (−)hydroxycitric acid that acts as an appetite suppressant and a lipid-lowering agent, as well as a fat burning agent. One way hydroxycitrate (HCA) present in the fruit rind of *Garcinia* species reduces weight gain is by competitively inhibiting ATP-citrate lyase, the enzyme responsible for catalyzing the extramitochondrial cleavage of citrate to oxaloacetate and acetyl-CoA, a building block of fatty acid synthesis [U.S. Pat. No. 3,764,692]. The mode of action of HCA appears to center on its ability to slow the regeneration of acetyl CoA—the citrate cleavage enzyme outside the mitochondria in hepatic cells. The effect is to reduce the major source of carbon atoms available for the synthesis of triglycerides, cholesterol and storage of fat without reduction in energy output. Carbon atoms are instead directed to glycogen in the muscles and liver, resulting in more stamina and increased endurance, but not increased body weight. Therefore, HCA is considered to be an effective herbal medicine for controlling obesity and cholesterol by inhibiting lipogenesis in the body.

HCA has also been demonstrated to cause weight loss in rodents by a reduction in food intake rather than through a direct effect on fatty acid synthesis. HCA improves synthesis of glycogen. Increased glycogen levels in the liver and muscles result in reduced appetite and food intake. In an animal study it was concluded that treatment with *Garcinia cambogia* fruit extract resulted in reduction of both serum and liver lipid to near normalcy. This hypolipidemic property of *Garcinia cambogia* in turn reduces the peroxidative damage, enhanced by ethanol [Mahendran et al 2001]. In a double-blind, Randomized, Placebo-Controlled trial it was observed that *Garcinia cambogia* extract had significantly reduced visceral, subcutaneous and total fat areas compared with placebo group [Hayamizu et al 2003]. Therefore, *Garcinia cambogia* extract is also considered a fat burning agent.

The sodium salt of hydroxycitric acid was studied by the Roche company in the 1970's and was shown to reduce food intake and cause weight loss in rodents. [Sullivan C, 1977] Subsequently, Heymsfield et al. evaluated the calcium salt of hydroxycitric acid in a human clinical trial and found it to be ineffective for weight loss, but failed to measure blood levels. [Heymsfield, S B et al.1998] The calcium salt of hydroxycitric acid used by Heymsfield may dissociate poorly and may not be absorbed and if so, poor absorption would explain the lack of efficacy in the Heymsfield study. Preuss et al. have published an abstract in which a mixture of calcium and potassium hydroxycitrate was used in a human clinical weight loss trial and was shown to be effective. [Preuss H. G., et al. 2002] Blood levels confirmed absorption of this hydroxycitrate compound. [Loe Y C et al. 2001, Loe Y C et al. 2001]

In various embodiments, the *Garcina* extract used in the weight loss composition described herein includes tri-, tetra-, or penta-metal complex salts of hydroxycitric acid. In an embodiment, the present invention provides a composition comprising a complex metal salt of (−)hydroxycitric acid either alone or in combination with the lactone of HCA and citric acid, wherein the salt comprises mineral supplements such as sodium, potassium, calcium, magnesium and zinc. The HCA complex metal salt is advantageously highly soluble in water, non-hygroscopic and stable in solution. Thereby avoiding problems with poor disassociation and absorbtion. In alternative embodiments, single complex salts of HCA, such as (Ca,K,Mg,Zn) HCA are included in the composition in alternative to or in addition to the tri-, tetra-, or penta-metal complex salts of hydroxycitric acid.

In another embodiment, the complex metal salt of HCA can be manufactured by keeping the pH of the final product, below 4, in which case the product will contain a combination of HCA and the lactone of HCA. This low pH embodiment can be formulated in carbonated beverages in which the pH is maintained below 4 for stability and is suitable for use in food products without affecting their flavor or taste.

The complex metal salt of (−)hydroxycitric acid is prepared from water extract of *Garcinia* and a mixture of bases selected from oxides, bicarbonates, carbonates, hydroxides of sodium, potassium, calcium, magnesium and zinc. Hydroxycitric acid is a tricarboxylic acid and therefore each HCA molecule can have only up to three different cations. However, some cations (such as the divalent cations. $Ca^{++}$ and $Mg^{++}$) can bond with two different molecules of hydroxycitric acid. Therefore, complex tetra or penta salts can be created using various cations and hydroxycitric acid. In some embodiments, the complex metal salt of hydroxycitric acid consists of two classes of cations, at least one bivalent ion—selected from Calcium (Ca), Magnesium (Mg) and Zinc (Zn) and at least one univalent ion—selected from Potassium (K) and Sodium (Na).

Embodiments of the complex metal salt of HCA can be prepared conveniently as highly soluble, partially soluble, or insoluble salt in water.

A representative general structure of complex salt of HCA is

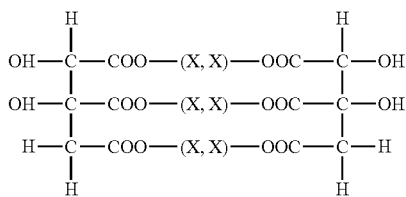

where (X,X) is selected from (Ca), (Mg), (Zn), (K,K), (Na, Na), (K, Na).

One particular representative example of four salt of Hydroxycitric acid is

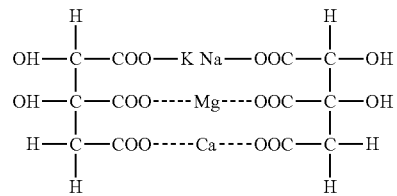

One particular representative example of three salt of Hydroxycitric acid is

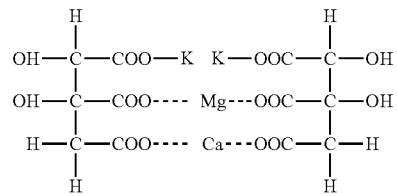

Five salt of *Garcinia* acid occurs when the terminal acid groups are bound with one univalent ion and one bivalent ion thereby giving room to the binding of third HCA molecule to the vacant bivalent ion.

One embodiment of complex metal salt of HCA that is essentially non-hygroscopic and stable in solutions includes (by weight percent) 40-75% (−)hydroxycitric acid (HCA) and/or 0.1-30% lactone of (−)hydroxycitric acid, 1-5% citric acid, 1-10% sodium (or alternatively less than 1%), 1-35% Potassium, 1-2% Calcium, 1-15% Magnesium, and 0.1-10% Zinc.

Embodiments of the complex metal salt of (−)hydroxycitric acid and/or its lactone can be manufactured by an economically viable process. In one embodiment, the *Garcinia* rind is extracted with demineralized water at room temperature. In contrast, the boiling or hot extraction used in the art gives an extract liquid that is enriched with unwanted water soluble components. In an embodiment, the unwanted soluble matter is minimized by extracting the rind at room temperature. The extract liquid is treated with a calcium base to neutral pH to get insoluble calcium hydroxycitrate. The HCA content of this insoluble material is approximately 70%. If the neutralization is done at pH more than 7, the HCA content in the resulting insoluble salt will be 50-60%.

The insoluble calcium salt of HCA is mixed with water and 10% sulphurous acid. This step removed the calcium as insoluble calcium sulphite. The pH is maintained at 3.0 to 3.5 during this operation. The art employs phosphoric acid in which case calcium cannot be removed as insoluble salt because both HCA and phosphoric acids are weak acids and an exchange reaction will not take place. The filtrate liquid, light brown in color, is treated with the preferred mixture of metal bases to neutral pH, treated with activated charcoal, filtered and spray dried to get white to off-white complex metal salt of HCA with or without the lactone of HCA. The resulting product is highly soluble in water (more than 20%), non-hygroscopic and stable in solution. Additional description for preparation of complex metal salt. HCA from *Garcina* is presented in U.S. Application Publication No. US 2004-0259937 A1, herein incorporated by reference.

In an embodiment, the *Garcinia* extract is a multimineral salt of hydroxy citric acid (4-salt HCA), which is obtained from water extract of *Garcinia Cambogia* fruit. In one embodiment, the *Garcinia* extract (4-salt HCA) contains 60 to 65% HCA bound to Ca, K, Mg and Zn moieties. The 4-salt HCA is non-toxic, tasteless, and odorless powder.

2. Banaba (5% Corosolic Acid)

Banaba whose botanical name is *Lagerstroemia speciosa* is a plant that is found in India, The Philippines, and parts of South East Asia. The plant has been traditionally used in the Philippines to treat diabetes and obesity. Banaba extracts have been found to assist in weight loss. In an animal study conducted by Suzuki, et al. it was shown that Banaba extracts induced weight loss and reduced adipose tissue weight. [Suzuki Y et al. 1999] Additionally, a significant drop of up to 65% in hepatic lipids was observed. Extracts of Banaba leaves containing a triterpene compound called Corosolic acid (2-hydroxyursolic acid) have demonstrated the capability to increase glucose uptake and lower blood sugar levels. Murakami et al. showed that Corosolic acid extracted from Banaba leaves stimulate significant glucose transport activity in vitro in Ehrlich ascites tumor cell studies. [Murakami C et al. 1993] Tommasi et al. reported the hypoglycemic action of Corosolic acid. [Tommasi N D et al. 1991] In an 8-week human clinical study conducted in Japan with 26 subjects, it was confirmed by Ikeda et al. that Corosolic acid improved glucose tolerance and improved blood sugar levels. [Ikeda Y et al. 1999] The same study also found that intake of Banaba extract was not harmful to any of the subjects.

3. Extract Of Green Coffee (Coffee Robusta 25% Chlorogenic Acid)

Green Coffee containing phenolic compounds called Chlorogenic acids may have the ability to assist in weight loss by blocking the uptake of carbohydrates. In a human clinical trial Johnston K L et al. evaluated Chlorogenic acids and found that they have an antagonistic effect on glucose absorption in the intestine. [Johnston K L et al. 2003] Chlorogenic acids may also induce weight loss inhibiting glucose creation from the metabolism of carbohydrates, thus inducing higher rates of metabolism in the body. In support of this hypothesis, Arion W J et al. and Hemmerle H et al. showed that Chlorogenic acids inhibit glucose-6-phosphate thereby curtailing the formation of glucose that is formed from gluconeogenesis and glycogenolysis. [Arion W J, et al. 1997, Hemmerle H, et al. 1997]

Tea and coffee are the most widely consumed beverages in the world next to water [Schaefer et al 2004]. Caffeine present in tea and coffee has been shown to increase energy expenditure in humans, and weight loss has reduced risk factors for diabetes in, clinical trials [Dulloo et al 1999; Bracco et al 1995]. Caffeine ingestion can acutely reduce glucose storage, but beneficial effects of caffeine on lipid oxidation and uncoupling protein-3 expression have also been suggested.

Coffee contains numerous substances; among them, caffeine, chlorogenic acids, quinides, and magnesium have been shown to affect glucose metabolism in animal or metabolic studies. In a Dutch study, it has been shown that higher coffee consumption was associated with a substantially lower risk of type 2 diabetes. Coffee is the major source of the chlorogenic acids. Intake of chlorogenic acids have been shown to reduce glucose concentrations in rats, and intake of quinides, degradation products of chlorogenic acids, increased insulin sensitivity in rats. Chlorogenic acids contribute to the antioxidant effects of coffee, may reduce hepatic glucose output through inhibition of glucose-6-phosphatase, and may improve tissue mineral distribution through its action as a metal chelator. In addition, chlorogenic acids act as a competitive inhibitor of glucose absorption in the intestine.

Recently, coffee consumption and type 2 diabetes has been reviewed by R. M. van Dam et al [R M Van Dam et al 2005]. The authors systematically reviewed all available epidemiological evidence on the relation between habitual coffee consumption and risk of type 2 diabetes. The authors conclude that their systematic review supports the hypothesis that habitual coffee consumption is associated with a substantially lower risk of type 2 diabetes.

4. Extract Of Green Tea (20% L-Theanine, 35% Polyphenols, 15% EGCG)

Green Tea leaves contain 1-2% by weight of an L-enantiomer stereoisomer of an amino acid. This amino acid is called Theanine and the L-enantiomer stereoisomer is referred to as L-Theanine. Extracts of Green Tea (*Camellia sinensis*) containing higher concentrations of L-Theanine may have the ability to assist in weight loss by reducing stress. L-Theanine's stress reducing capabilities are well documented. In human clinical trials, Mason R et al. found that L Theanine stimulates the production of alpha brain waves thereby creating a sense of alertness and relaxation. [Mason R. 2001] It was also found that L-Theanine is involved in the formation of gamma amino butyric acid (GABA). This leads to a relaxation effect as GABA influences the levels of the neurotransmitters, dopamine and serotonin. In another clinical trial Juneja L R et al. confirmed that L-Theanine increase alpha brain wave activity. [Juneja L R 1999]

Oral administration of green tea extract rich in catechin polyphenol and caffeine stimulates thermogenesis and fat oxidation and thus has the potential to influence body weight and body composition via changes in both energy expenditure and substrate utilization. In particular, tea polyphenol have been suggested to play a role in lowering the oxidation of low density cholesterol (LDL), with a consequent decreased risk of heart disease [Weisburger, 1999]. In a cross-cultural correlation study of sixteen cohorts, known as the Seven Countries Study, the average flavanol intake was inversely correlated with mortality rates of coronary heart disease after 25 years of follow-up. [Hertog et al., 1995; Hollman et al., 1999]

5. Safety Of *Garcinia* Extract 4-Salt HCA And The Other Extracts

*Garcinia* has been used in foods as a seasoning for many years. There have been several clinical trials showing it to be safe in acute administration at doses as high as 6-30 times the dose used in diet supplements and in extended doses in obese and overweight subjects. [Preuss, H. G. et al. 2004, van Loon, L. et al. 2000, and Heymsfield, S. 1998] Cantox Health Sciences International, Missisauga, ON Canada, was commissioned by Indfrag Limited to do a safety assessment of HCA. After reviewing all the pertinent scientific literature Cantox found no relevant safety issues at doses in the range of 1 to 5 grams a day. HCA has been used for many years in supplements without significant adverse effects.

The safety of Banaba extract is reinforced by the fact that it has been traditionally used in the Philippines for many years. Shirai et al. confirmed Banaba's safety in an in vivo, mouse model. [Shirai M. et al. 1994] Green Coffee extract has a history of safe usage as a food ingredient. L-Theanine has a history of safe usage as a dietary supplement.

6. Herbal Composition

One embodiment of the herbal composition of the present invention is presented in Table 1. The herbal composition may additionally comprise pharmaceutically acceptable excipients.

TABLE 1

An Embodiment of the Herbal Composition of Present Invention Expressed as Range of Proportion of Extracts

| Name of the botanical extract | Daily Adult Dose | Approx. wt % in composition |
|---|---|---|
| Garcinia extract | 1950 mg to 4875 mg | 55% to 88% |
| Green tea extract | 225 mg to 600 mg | 4% to 19% |
| Green coffee extract | 345 mg to 865 mg | 6% to 28% |
| Banaba extract | 75 mg to 190 mg | 1% to 7% |

One embodiment of the herbal composition includes a daily dose of about 3900 mg Garcinia 4 salt-HCA, 450 mg Green coffee extract (25% chlorogenic acids), 600 mg Green Tea extract (25% L-Theanine and 35% Polyphenols: 15% EGCG), 150 mg Banaba extract (5% Corosolic acid).

The composition of the present invention, in addition to the active ingredients noted in Table 1 above, may also contain pharmaceutical excipients that are usually employed to prepare any oral dosage form such as powder, tablets, capsules, syrups, and liquids etc.

The excipients, such as starch, pre-gelatinized starch, dicalcium phosphate, polyvinyl povidine, magnesium stearate, talc, ethanol, isopropanol, or other alcohols, carboxymethyl cellulose, hydroxymethylcellulose, ethyl cellulose or other cellulose materials or a mixture thereof may be used. A suitable amount of excipient is employed for formation of the selected oral delivery form. The composition may also contain preservatives, which may be selected from parabens, including paraben salts such as propylparaben sodium and methyl paraben sodium, or 2-bromo-2-nitropropane-1,3-diol (BRONOPOL) or a mixtures thereof.

The Daily Adult Dose presented in Table 1 may be divided into multiple doses administered at time intervals, throughout a 24 hour interval. In various embodiments, the daily dose is divided for administration as one, two, three, four, five, or six doses per day. In a further embodiment, the daily dose is orally administered in two divided doses of 2 caplets per dose. In an embodiment, the herbal composition is administered 30-60 minutes before a meal.

Table 2 gives the proportion of the extracts in one embodiment of a tablet or capsule made by mixing the herbal extracts. Two to five tablets or capsules illustrated in Table 2 would provide an adult daily dose. The tablets or capsules are administered in one or more divided doses. In one embodiment, the divided doses are administered from between 2 hours to 30 minutes before one or more meals within a day.

TABLE 2

An Embodiment of the Herbal Composition of Present Invention Expressed as Specific Proportion of Extracts

| Name of the botanical extract | mg per tablet or capsule | Approx. % by weight of active ingredients |
|---|---|---|
| Garcinia extract | 975 mg | 76.5% |
| Green tea extract | 150 mg | 11.8% |
| Green coffee extract | 112 mg | 8.8% |
| Banaba extract | 37 mg | 2.9% |
| Excipients | q.s. | — |

The compositions provided above are dependent on the content of the individual extracts, as described below. As is understood, the quantity of an extract included in the present herbal composition is adjusted based on the potency of the individual extract. Alternatively, an extract is standardized according to the contents described below for use in the present herbal composition.

Garcinia extract contains greater than 60% (−)hydroxycitric acid, less than 5% lactone of (−)hydroxycitric acid, less than 5% citric acid, 4-6% calcium, 4-6% potassium, 8-10% magnesium, 0.4-0.6% zinc and less than 1% sodium. A unique (−) hydroxycitric acid composition is described and claimed in published US patent application US 2004/0259937 herein incorporated by reference. The (−)hydroxycitric acid composition contains 40-75% (−)hydroxycitric acid, 0.1-30% lactone of (−) hydroxycitric acid, 1-5% citric acid, 1-10% sodium, 1-35% potassium, 1-20% calcium, 1-15% magnesium and 0.1-10% zinc.

In one embodiment of the invention, the content of calcium in the Garcinia extract is 20-80 mg per gram of complex metal salt of HCA. In another embodiment, the content of magnesium is 60-100 mg per gram of complex metal salt of HCA. In yet another embodiment, the content of potassium is 20-100 mg per gram of complex metal salt of HCA. In yet another embodiment, the content of zinc is 2-6 mg per gram of complex metal salt of HCA.

The active ingredients in the full spectrum Green tea extract are catechin polyphenols, caffeine, L-theanine and other amino acids. The compositions provided herein utilize a unique full spectrum green tea extract containing greater than 35% polyphenols in which greater than 15% is EGCG, as well as containing approximately 11-13% Caffeine, L-theanine 21-23%.

The active ingredients in the full spectrum extract of green coffee are chlorogenic acids, caffeine and polyphenols. The present invention utilizes a unique full spectrum coffee extract containing a minimum of 25% chlorogenic acids, 1-2% caffeine and greater than 40% polyphenols.

Banaba extract in the present invention contains 5% corosolic acid along with other biologically active constituents.

All the extracts are produced using water or aqueous methanol as solvent. The extract are mixed in the above said proportion along with excipients appropriate for the selected delivery form, in a high speed blender to get uniformity in terms of color and active ingredient. The resulting blend is then tableted, encapsulated or provided in powdered or liquid/syrup form.

In an embodiment consistent with that presented in Table 2 above, the active ingredient contents per tablet is summarized in table 3.

TABLE 3

Active Ingredients Per Tablet

| Name of the active ingredient | mg of active ingredient per tablet |
|---|---|
| (−)Hydroxycitric acid | 600-660 mg |
| Polyphenol | 90-100 mg |
| EGCG | 23-30 mg |
| Caffeine | 18-22 mg |
| L-theanine | 35-40 mg |
| Chlorogenic acids | 25-35 mg |
| Colosolic acid | 2-3 mg |
| Calcium | 55-65 mg |

HCA, EGCG, Caffeine, L-theanine, Chlorogenic acids and Colosolic acid present in the composition are estimated using High pressure Liquid chromatography (HPLC). Polyphenols are estimated by UV method.

The present invention is described in further detail in the following clinical experiments, which are merely exemplary and are not intended to limit the scope of the invention.

7. Example: Efficacy and Safety Study of Active HCA and Active HCA 7.1 Summary

A three-group, parallel, double-blind, randomized, prospective, placebo-controlled, efficacy and safety study was completed to test the weight-reduction effects of Garcinia extract 4-salt HCA (active HCA), and a combination of Garcinia extract 4-salt HCA, Banaba extract, Green Coffee extract, and Green Tea extract (herbal composition) in healthy overweight and obese adults over a 12-week period. Products evaluated during this study are shown in Table 4.

The per-protocol patient population consisted of 91 subjects of Asian ethnicity with BMI values between 28 and 40 kg/m². Two-thirds of the patient population were male. One-third of the patient population was female. The ages of the patient population varied from 19 to 58 years of age with a mean age in the mid-to-late thirties. The patients activity level at work ranged from sedentary to heavy.

Patients were randomized between three treatment arms (1:1:1 ratio) and received either Herbal Composition, Active HCA or Placebo for 12 weeks. Study endpoints were evaluated at weeks 0, 2, 4, 6, 8, 10, and 12.

The following products were evaluated. The composition was developed by Indfrag Ltd. with technical assistance from Dr. Fred Pescatore, MD, MPH, CCN. The supplements used in the trial were produced and certified to contain the active ingredients, in the dose specified, by the manufacturer and sponsor of the trial, Indfrag Limited, 1320, 12 Cross, Indiranagar II Stage, Bangalore 560-038, India. Each lot that was individually assayed and the quality of the extracts was ensured by Certificates of Analysis provided by Indfrag Ltd

TABLE 4

Products Evaluated During Study

| Product | Active Formula | Active HCA | Placebo |
|---|---|---|---|
| Contents | Garcinia extract 4-salt HCA Banaba Extract Green Coffee Extract Green Tea Extract | Garcinia extract 4-salt HCA | Cellulose Maltodextrin |

The primary efficacy endpoint of the study was reduced fat mass on the dual energy x-ray absorptiometry (DEXA) scan between baseline and 12 week visit and loss of 5% or more of body weight at 12 weeks.

The secondary efficacy endpoints of the study were: improved body composition, increase lean Mass and improved bone density measured by dual energy x-ray absorptiometry (DEXA) scan; reduced abdominal girth; improved lipid profiles; reduced insulin resistance calculated by the HOMA-IR method, ability to maintain a weight loss diet and/or diminished appetite; and improved quality of life based on a quality of life questionnaire (QLQ).

The primary safety endpoints were physical examination (HR, SBP, DBP) and safety laboratory values (Complete Blood count (CBC), BUN, electrolytes, glucose, creatinine, calcium, AST, ALT, Alkaline Phosphatase, total bilirubin, uric acid, urine analysis, cholesterol, triglycerides, TSH, HbA1c, pregnancy test (females), amylase). The secondary safety endpoint was adverse events.

It was found that the significant reduction in body fat and significant body weight loss of 6.18% by the active formula group met the primary efficacy objectives of the study.

On analyzing the efficacy data for the active HCA it was found that body fat reduced significantly thus meeting a primary efficacy objective. Though body weight reduced significantly, the reduction of only 2.91% was not enough to meet the primary efficacy objective of a 5% body weight reduction.

In addition, the active formula group and active HCA groups also showed a significant reduction in abdominal girth which was listed as a secondary efficacy objective.

Furthermore, both active groups also showed a decrease in diastolic blood pressure and AST broadly indicating an improving metabolic profile.

No serious adverse events were noted in this study.

7.2 Efficacy Analysis 7.2.1 Changes in Efficacy Variables from Baseline to End of Study (Per-Protocol Analysis)

Figure 2:
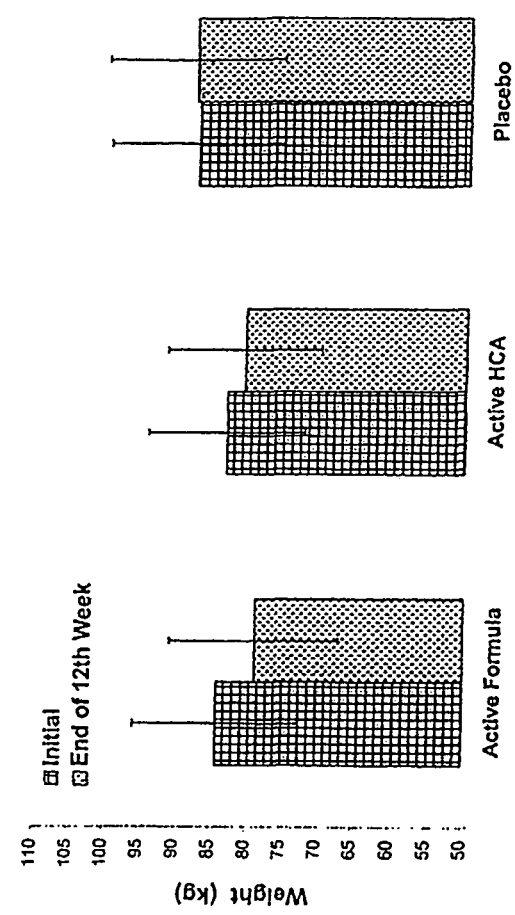
FIG. 2. is a graphical representation of the change in mean body weight between baseline and end of study for all three groups.

Tables 5-13 and FIGS. 1 and 2 (graphs plotted for Primary efficacy variables of fat mass and body weight only) summarize the change in efficacy variables from baseline to end of study (week 12) for each product group. Baseline is defined as the average of available values from the screening and/or randomization visit (prior to dispensation of study product).

Variables are summarized in the format:

Mean±Standard Deviation

Referring to Tables 5-13, the p-values at the row titled 'significance (Baseline-12$^{th}$ week)' of each table indicates whether that product group had a significant average change from baseline—this was calculated using the paired student t test with Bonferroni correction. The p-values in the last column of the table with the heading 'Significance comparisons' indicates whether the amount of change was significantly different between the active and placebo groups calculated by ANCOVA (Pre values are the covariates and the significance is calculated on the difference of post values). Nominally significant p-values ($p<0.05$) are highlighted in bold text. The significance data between active groups and the placebo group is indicated in the row titled 'Significance of Active Group compared with Placebo'. For the lipid profile table non-identical superscripts are significant at $p<0.05$, identical superscripts are not significant using the Student t test with Bonferroni correction.

The estimate of effect size was computed using the partial Eta square method for all groups for all primary efficacy variables and selected secondary efficacy variables. The effect size for each group is indicated in the row titled 'Estimate of Effect' for each respective table.

The graphs represent the change in means in all three groups from the baseline to the end of study. The standard deviations were calculated for all the means displayed here, and the standard deviation bars are displayed on the graphs.

This summary is based on the per-protocol population, consisting of all subjects who kept all scheduled visits and who were at least 75% product compliant over the 12-week course of the study. A per-protocol analysis addresses the scientific question of whether the product works in those people who use it as directed. Subjects who do not take the product as directed, or who drop out of the protocol, have not really given the product a "fair chance" of working. Evaluating whether the product is efficacious, a per-protocol analysis therefore looks only at data from those subjects who were compliant with the protocol.

Changes In Efficacy Variables (Per-Protocol Population)
Primary Efficacy Variables

TABLE 5

Fat Mass (see related FIG. 1.)

| Study period | Fat mass in gms | | |
|---|---|---|---|
| | Active formula (n = 30) | Active HCA (n = 32) | Placebo (n = 29) |
| Baseline | 32810.37 ± 7024.79 | 30942.46 ± 5916.88 | 33399.41 ± 8457.21 |
| End of 12$^{th}$ week | 31107.42 ± 7068.24 | 30245.18 ± 6188.14 | 33697.18 ± 8437.30 |
| Difference in Fat mass loss (grams) | 1702.95 | 697.28 | −297.77 |
| Significance (Baseline-12$^{th}$ week) | p < 0.001 | p < 0.01 | p = 0.293 |
| Significance of Active Group compared with Placebo by ANCOVA | p < 0.001 | p = 0.011 | — |
| Estimate of Effect | 67.7% | 19.6% | 3.9% |

TABLE 6

Body Weight (see related FIG. 2.)

| Study period | Body Weight in kg | | |
|---|---|---|---|
| | Active formula (n = 30) | Active HCA (n = 32) | Placebo (n = 29) |
| Baseline | 84.20 ± 11.64 | 83.07 ± 10.92 | 87.63 ± 12.14 |
| End of 12$^{th}$ week | 78.99 ± 11.95 | 80.65 ± 10.80 | 87.98 ± 12.26 |
| Difference in weight loss (kg) | 5.21 | 2.42 | −0.35 |
| Significance (Baseline-12$^{th}$ week) | p < 0.001 | p < 0.001 | p = 0.222 |
| Significance of Active Group compared with Placebo | p < 0.001 | p < 0.001 | — |
| Estimate of Effect | 76.1% | 53.2% | 4.5% |

Secondary Efficacy Variables

TABLE 7

Lean Mass

| Study period | Lean mass in gms | | |
|---|---|---|---|
| | Active formula (n = 30) | Active HCA (n = 32) | Placebo (n = 29) |
| Baseline | 46388.46 ± 9334.98 | 47389.06 ± 10755.03 | 49707.05 ± 8748.72 |
| End of 12$^{th}$ week | 45668.29 ± 9255.95 | 46769.06 ± 10049.42 | 49077.05 ± 8446.49 |
| Difference in Lean mass loss (grams) | 720.17 | 620 | 630.00 |
| Significance (Baseline-12$^{th}$ week) | p = 0.075 | p = 0.044 | p = 0.087 |
| Significance of Active Group compared with Placebo | p = 0.651 | p = 0.729 | — |

TABLE 8

Bone Density

| Study period | Bone Density in gms | | |
|---|---|---|---|
| | Active formula (n = 30) | Active HCA (n = 32) | Placebo (n = 29) |
| Baseline | 1.144 ± 0.102 | 1.154 ± 0.119 | 1.205 ± 0.143 |
| End of 12$^{th}$ week | 1.154 ± 0.087 | 1.151 ± 0.111 | 1.203 ± 0.131 |
| Difference in Bone Density (gms) | −0.01 | 0.003 | 0.002 |
| Significance (Baseline-12$^{th}$ week) | p = 0.549 | p = 0.487 | p = 0.747 |
| Significance of Active Group compared with Placebo | p = 0.692 | p = 0.377 | — |

TABLE 9

Abdominal Girth

| Study period | Abdominal girth in cms | | |
|---|---|---|---|
| | Active formula (n = 30) | Active HCA (n = 32) | Placebo (n = 29) |
| Baseline | 98.90 ± 13.40 | 99.28 ± 12.17 | 100.50 ± 13.39 |
| At 12 weeks | 94.50 ± 13.07 | 95.73 ± 11.61 | 99.78 ± 13.67 |
| Difference in Girth change (cm) at 12 weeks | 4.40 | 3.55 | 0.72 |
| Significance (Baseline-12$^{th}$ week) | p < 0.001 | p < 0.001 | p = 0.529 |
| Significance of Active Group compared with Placebo | p < 0.001 | p = 0.002 | — |
| Estimate of Effect | 42.7% | 38.4% | 3% |

TABLE 10

Lipid Profile

| Lipid Parameters | | Active formula (n = 30) | Active HCA (n = 32) | Placebo (n = 29) |
|---|---|---|---|---|
| Total cholesterol | Baseline | 181.97 ± 25.64$^a$ | 172.00 ± 29.52$^a$ | 183.93 ± 30.68$^a$ |
| | At 12 weeks | 185.43 ± 25.69$^a$ | 182.35 ± 27.32$^b$ | 192.79 ± 31.81$^a$ |
| Triglycerides | Baseline | 155.30 ± 40.42$^a$ | 155.25 ± 45.19$^a$ | 164.41 ± 62.39$^a$ |
| | At 12 weeks | 157.90 ± 52.02$^a$ | 150.87 ± 51.21$^a$ | 164.21 ± 83.83$^a$ |

TABLE 10-continued

Lipid Profile

| Lipid Parameters | | Active formula (n = 30) | Active HCA (n = 32) | Placebo (n = 29) |
|---|---|---|---|---|
| LDL | Baseline | 112.33 ± 18.87$^a$ | 103.94 ± 25.71$^a$ | 113.07 ± 26.77$^a$ |
| | At 12 weeks | 114.17 ± 20.95$^a$ | 115.39 ± 25.95$^b$ | 122.14 ± 27.62$^a$ |
| VLDL | Baseline | 30.78 ± 8.03$^a$ | 30.95 ± 9.05$^a$ | 32.71 ± 12.47$^a$ |
| | At 12 weeks | 38.30 ± 10.40$^a$ | 30.33 ± 10.16$^a$ | 32.52 ± 15.89$^a$ |
| HDL | Baseline | 38.30 ± 7.06$^a$ | 35.93 ± 8.14$^a$ | 37.83 ± 6.16$^a$ |
| | At 12 weeks | 38.37 ± 7.34$^a$ | 36.45 ± 7.25$^a$ | 36.59 ± 6.14$^a$ |

TABLE 11

HOMA-IR

| Study period | Active formula (n = 30) | Active HCA (n = 32) | Placebo (n = 29) |
|---|---|---|---|
| Baseline | 4.22 ± 2.33 | 4.15 ± 2.37 | 4.26 ± 3.03 |
| End of 12$^{th}$ week | 4.71 ± 2.79 | 4.18 ± 2.59 | 5.85 ± 3.60 |
| Difference in HOMA-IR | 1.68 | 0.16 | 1.59 |
| Significance (Baseline-12$^{th}$ week) | p = 0.238 | p = 0.951 | p = 0.009 |
| Significance of Active Group compared with Placebo | p = 0.107 | p = 0.030 | — |

TABLE 12

Appetite Test

| Study period | Active formula (n = 30) | Active HCA (n = 32) | Placebo (n = 29) |
|---|---|---|---|
| Baseline | 7.47 ± 3.87 | 8.58 ± 3.83 | 8.94 ± 3.98 |
| End of 12$^{th}$ week | 5.87 ± 2.37 | 6.69 ± 3.63 | 7.90 ± 4.19 |
| Difference in Appetite test (VAS) | 1.6 | 1.51 | 1.04 |
| Significance (Baseline-12$^{th}$ week) | p < 0.001 | p < 0.001 | p = 0.077 |
| Significance of Active Group compared with Placebo | p = 0.080 | p = 0.301 | — |

TABLE 13

Quality of Life (Total Score)

| Study Period | Active formula (n = 30) | Active HCA (n = 32) | Placebo (n = 29) |
|---|---|---|---|
| Initial | 34.50 ± 16.94 | 35.22 ± 25.55 | 32.41 ± 22.86 |
| At the End of 12$^{th}$ week | 28.43 ± 12.88 | 29.88 ± 27.01 | 28.33 ± 21.65 |
| Difference in Quality of Life (Total score) | 6.07 | 5.34 | 4.08 |
| Significance (Baseline-12$^{th}$ week) | p = 0.043 | p = 0.051 | p = 0.116 |
| Significance of Active Group compared with Placebo | p = 0.684 | p = 0.808 | — |

When examining the baseline data it was found that the groups when compared with each other did not show any significant differences as calculated by ANOVA. At the end of the study the tables were analyzed again using ANCOVA to see if there were any differences from the baseline for all three groups. The data from this analysis is displayed below:
  a. Fat Mass—F=15.309 and p<0.001
  b. Body Weight—F=118.03 and p<0.001

Thus, it can be concluded that there were significant changes in the primary efficacy variables between all three groups from baseline to the end of study.

On analyzing the variables in each group it was found that four of the primary efficacy variables underwent statistically significant changes from baseline to end of study:
  a. 1702.95 gms decrease in fat mass in Active formula group
  b. 697.28 gms decrease in fat mass in Active HCA group
  c. 5.21 kg or 6.18% decrease, in body weight in Active formula group
  d. 2.42 kg or 2.91% decrease in body weight in Active HCA group The active formula group as well as the active HCA group showed a significant reduction in fat mass and body weight when compared with the placebo group.

The placebo group showed slight but statistically insignificant increases in fat mass and body weight.

Looking at the estimate of effect analysis for fat mass it was found that the active formula had the best reliability factor (67.7%) followed by the active HCA (19.6%) and placebo (3.9%). Thus it can be concluded that the active formula has a higher chance for inducing fat mass loss than the active HCA and placebo. It can also be concluded that the active HCA has a higher chance for inducing fat mass loss than the placebo.

Similarly, looking at the estimate of effect analysis for body weight it was found that the active formula had the best reliability factor (76.1%) followed by the active HCA (53.2%) and placebo (4.5%). Thus it can be concluded that the active formula has a higher chance for inducing weight loss than the active HCA and placebo. It can also be concluded that the Active HCA has a higher chance for inducing weight loss than the placebo.

Further analysis was carried out on the body weight variable as data was collected at 2 week intervals and not only at the baseline and end of study. This was also tabulated and represented in table 13 below. It was found that the change in body weight was linear for the active formula and active HCA groups while it was non-linear for the placebo group as calculated by Repeated Measures ANOVA.

When examining the baseline data it was found that the groups when compared with each other did not show any significant differences as calculated by ANOVA. At the end of the study the tables were analyzed again using ANCOVA to see if there were any differences from the baseline for all three groups (as the lipid profile variables did not show changes of clinical significance the ANCOVA analysis was not done for these variables). The data from this analysis is displayed below:

a. Lean Mass—F=0.176 and p=0.839
b. Body Density—F=0.632 and p-0.534
c. Abdominal Girth—F=8.574 and p<0.001
d. HOMA-IR—F=3.23 and p=0.049
e. Appetite test—F=1.089 and p=0.19
f. Quality of Life Questionnaire—F=0.097 and p=0.908

Thus, it can be concluded that there was a significant change in the abdominal girth and the HOMA-IR variables between all three groups from baseline to the end of study. None of the other secondary efficacy variables showed any significance between all three groups from baseline to the end of the study.

On analyzing the variables in each group it was found that nine of the secondary efficacy variables underwent statistically significant changes from baseline to end of study:

a. 620 gms decrease in Lean Mass in Active HCA Group
b. 4.40 cms decrease in abdominal girth in Active formula group
c. 3.55 cms decrease in abdominal girth in Active HCA group
d. 10.35 mg/dL increase in total cholesterol in Active HCA group
e. 11.45 mg/dL increase in LDL in Active HCA group
f. 1.59 increase in HOMA-IR in placebo group
g. 1.6 unit decrease in the appetite test (VAS) in the Active formula group
h. 1.89 unit decrease in the appetite test (VAS) in the Active HCA group
i. 6.07 unit decrease in the Quality of Life Questionnaire in Active formula group The active Formula group showed a significant reduction in abdominal girth when compared with the placebo group.

Even though there was a significant decrease in the Quality of Life score (indicative of a better quality of life) and the Appetite test score (indicative of a reduced appetite) for the active formula group, when compared with placebo group this change was not significant.

The active HCA group showed a significant decrease in lean mass and appetite test score (Indicative of a reduced appetite), however when compared with the placebo group the changes were not significant.

The active HCA group also showed a significant reduction in abdominal girth when compared with the placebo group.

Finally, the active HCA group also showed an increase in Total Cholesterol and LDL. These changes observed were not clinically significant as the mean values for the Total Cholesterol and LDL are within the NCEP ATP III [National Cholesterol Education Program Expert Panel on Detection, Evaluation, and Treatment of High Blood Cholesterol in Adults (Adult Treatment Panel III), NIH Publication No. 02-5215, September 2002] guidelines for all three groups at the end of the study and furthermore, the comparison between these variables and the corresponding placebo variables were not statistically significant.

Even though the active HCA group did not show a significant change in HOMA-IR when compared with placebo there was a significant change. The active HCA has shown a relatively smaller increase in HOMA-IR (Increase of 0.03) than the placebo (Increase of 1.59), thus it can be concluded there is a possibility that the active HCA may arrest increases in HOMA-IR.

Looking at the estimate of effect analysis for abdominal girth it was found that the active formula had the best reliability factor (42.7%) followed by the active HCA (38.4%) and placebo (3%). Thus it can be concluded that the active formula has a higher chance for inducing a decrease in abdominal girth than the active HCA and placebo. It can also be concluded that the active HCA has a higher chance for inducing a decrease in abdominal girth than the placebo.

Further analysis was carried out on the abdominal girth variable as data was collected at 2 week intervals and not only at the baseline and, end of study. This was also tabulated and represented in Table 15 below. It was found that the change in abdominal girth was linear for the active formula and active HCA groups while it was non-linear for the placebo group as calculated by Repeated measures ANOVA.

7.2.2 Time-Course of Selected Efficacy Variables and Derived Efficacy Variables (Per-Protocol Population)

Figure 3:
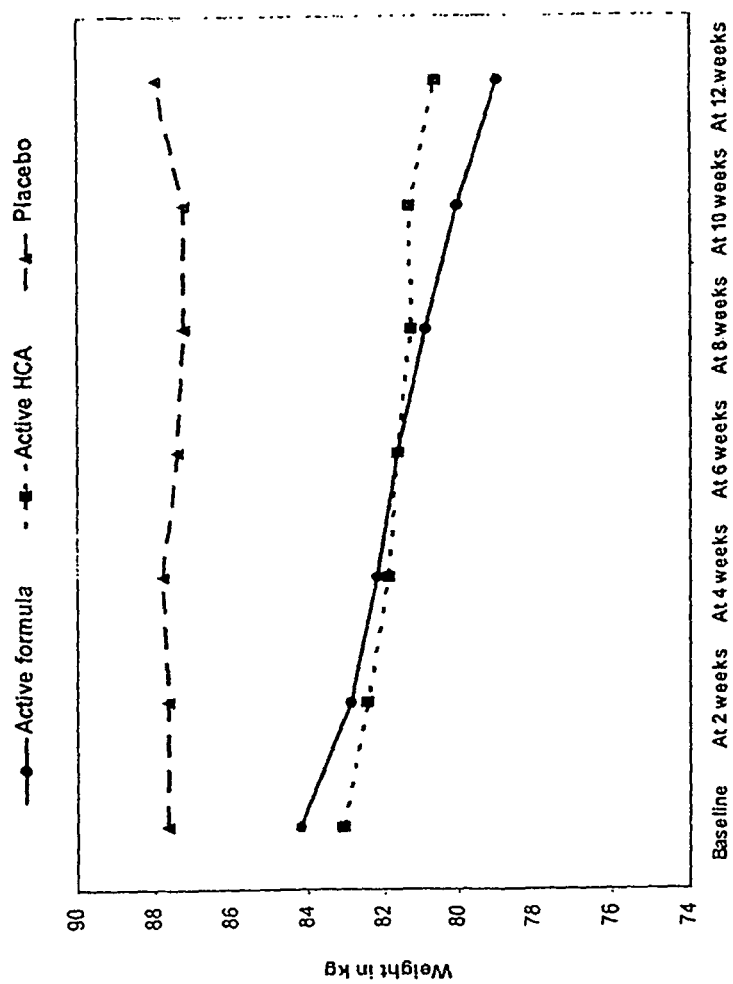
FIG. 3. is a graphical representation of the change in weight from baseline to end of study at each two-week interval for all three groups.
Figure 4:
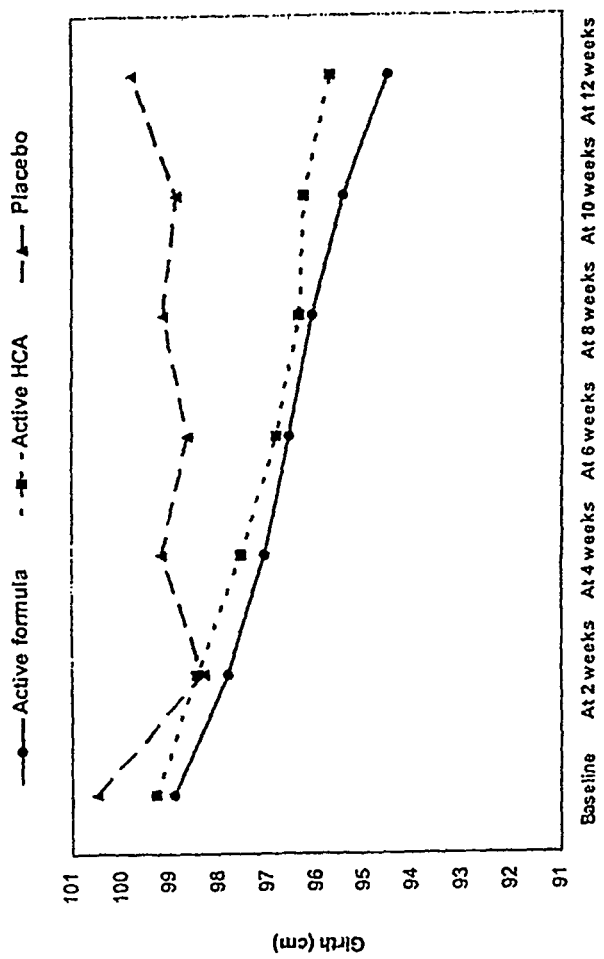
FIG. 4. is a graphical representation of the change in girth from baseline to end of study at each two-week interval for all three groups.
Figure 5:
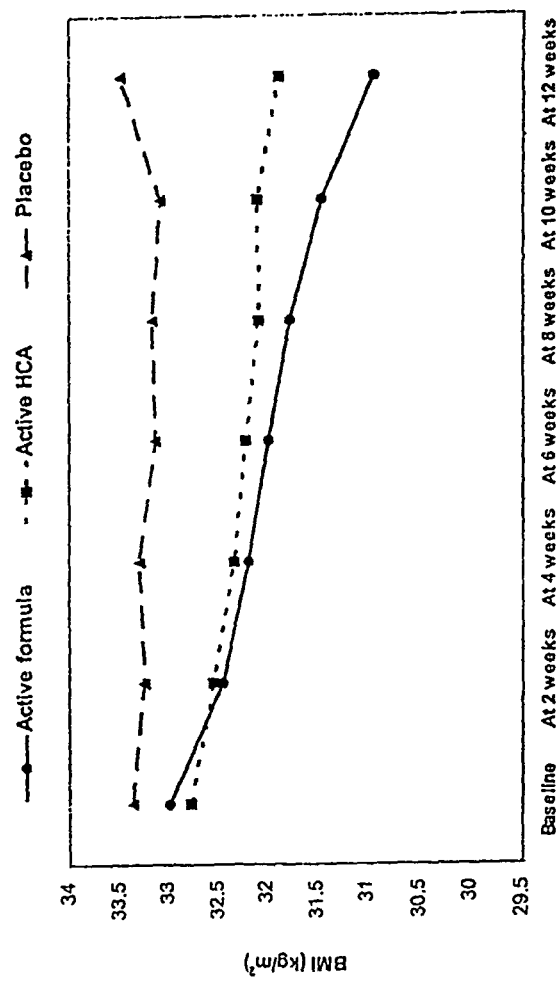
FIG. 5. is a graphical representation of the change in BMI from baseline to end of study at each two-week interval for all three groups.

Tables 14-16 and related FIGS. 3-5 display the visit-by-visit values of those efficacy variables that were collected at baseline (screening and/or randomization), two week intervals and end of the study. The change in Body Mass Index (BMI) was derived from the body weight and height data and the results are shown in Table 16 with inference and graph shown in FIG. 5.

Such tables and graphs are meaningful only for subjects who had values at all of theses time points, and were therefore based on the per-protocol population.

TABLE 14

Change in Weight from Baseline to End of Study at Each Two-Week Interval for All Three Groups (see related FIG. 3.)

| | Weight in kg | | |
|---|---|---|---|
| Study Period | Active formula (n = 30) | Active HCA (n = 32) | Placebo (n = 29) |
| Baseline | 84.20 ± 11.64 | 83.07 ± 10.92 | 87.63 ± 12.14 |
| At 2 weeks | 82.86 ± 11.86 | 82.44 ± 10.78 | 87.64 ± 12.59 |
| At 4 weeks | 82.19 ± 11.94 | 81.88 ± 10.67 | 87.82 ± 12.56 |
| At 6 weeks | 81.64 ± 11.79 | 81.61 ± 11.07 | 87.41 ± 12.32 |
| At 8 weeks | 80.89 ± 12.03 | 81.28 ± 11.19 | 87.26 ± 12.47 |
| At 10 weeks | 80.08 ± 12.09 | 81.32 ± 11.16 | 87.26 ± 12.75 |
| At 12 weeks | 78.99 ± 11.95 | 80.65 ± 10.80 | 87.98 ± 12.26 |
| Difference in weight loss (kg) at 12 weeks | 5.21 | 2.42 | −0.35 |

TABLE 15

Change in Girth from Baseline to End of Study at Each Two-Week Interval for All Three Groups (see related FIG. 4.)

| | Abdominal girth in cms | | |
|---|---|---|---|
| Study Period | Active formula (n = 30) | Active HCA (n = 32) | Placebo (n = 29) |
| Baseline | 98.90 ± 13.40 | 99.28 ± 12.17 | 100.50 ± 13.39 |
| At 2 weeks | 97.81 ± 12.79 | 98.44 ± 12.15 | 98.29 ± 13.65 |
| At 4 weeks | 97.07 ± 13.38 | 97.52 ± 11.87 | 99.19 ± 12.69 |
| At 6 weeks | 96.55 ± 13.38 | 96.82 ± 11.55 | 98.65 ± 13.45 |
| At 8 weeks | 96.10 ± 13.37 | 96.34 ± 11.48 | 99.16 ± 13.75 |
| At 10 weeks | 95.45 ± 13.41 | 96.26 ± 111.46 | 98.88 ± 14.07 |
| At 12 weeks | 94.50 ± 13.07 | 95.73 ± 11.61 | 99.78 ± 13.67 |
| Difference in Girth change (cm) at 12 weeks | 4.40 | 3.55 | 0.72 |

TABLE 16

Change in BMI from Baseline to End of Study at Each 2 Week Interval for All Three Groups (see related FIG. 5.)

| | BMI in kg/m² | | |
|---|---|---|---|
| Study Period | Active formula (n = 30) | Active HCA (n = 32) | Placebo (n = 29) |
| Baseline | 32.99 ± 2.68 | 32.77 ± 2.83 | 33.36 ± 3.72 |
| At 2 weeks | 32.44 ± 2.67 | 32.55 ± 2.87 | 33.24 ± 3.77 |
| At 4 weeks | 32.19 ± 2.78 | 32.33 ± 2.84 | 33.30 ± 3.74 |
| At 6 weeks | 31.98 ± 2.78 | 32.22 ± 2.89 | 33.14 ± 3.64 |
| At 8 weeks | 31.78 ± 2.73 | 32.09 ± 2.98 | 33.17 ± 3.79 |
| At 10 weeks | 31.47 ± 2.83 | 32.11 ± 2.92 | 33.09 ± 3.79 |
| At 12 weeks | 30.96 ± 2.79 | 31.89 ± 2.92 | 33.49 ± 3.72 |
| Difference in BMI change (kg) at 12 weeks | 2.06 | 0.88 | −0.13 |
| Significance (Baseline-12$^{th}$ week) | p < 0.001 | p < 0.001 | p = 0.216 |
| Estimate of Effect | 65.3% | 48.5% | 4.8% |

Interpretation for BMI

The active formula showed a significant drop in BMI of 2.06 kg/m². The active HCA showed a significant drop in BMI of 0.88 kg/m² and the placebo showed a slight but insignificant increase in BMI. The active formula and active HCA showed a significant change from baseline when compared with placebo as calculated by ANCOVA.

Looking at the estimate of effect analysis for BMI it was found that the Active formula had the best reliability factor (65.3%) followed by the Active HCA (48.5%) and placebo (4.8%). Thus it can be concluded that the Active formula has a higher chance for inducing a decrease in BMI than the Active HCA and placebo. It can also be concluded that the Active HCA has a higher chance for inducing a decrease in BMI than the placebo.

Further analysis was carried out on the BMI variable as data was collected at 2 week intervals and not only at the baseline and end of study. It was found that the change in BMI was linear for the active formula and active HCA groups while it was non-linear for the placebo group as calculated by Repeated measures ANOVA.

7.2.3 Efficacy Conclusions

It was found that the significant reduction in body fat and significant body weight loss of 6.18% by the active formula group met the primary efficacy objectives of the study.

On analyzing the efficacy data for the active HCA it was found that body fat reduced significantly thus meeting a primary efficacy objective. Though body weight reduced significantly, the reduction of only 2.91% was not enough to meet the primary efficacy objective of a 5% body weight reduction.

In addition, the active formula group and active HCA groups also showed a significant reduction in abdominal girth which was listed as a secondary efficacy objective.

Furthermore, the both active groups also showed a decrease in diastolic blood pressure and AST broadly indicating an improving metabolic profile.

7.3 Study Population and Baseline 7.3.1 Disposition of Subjects and Analytical Populations Out of 165 subjects who were screened, 49 were screen failures and 116 were randomized into the study.

These 116 subjects were randomized into three groups, using a randomization schedule supplied by the sponsor. The disposition of these subjects is shown in Table 17.

TABLE 17

Disposition of Enrolled Subjects

| Status of subjects | Active formula | Active HCA | Placebo | Total |
|---|---|---|---|---|
| Lost to follow up | 1 (2.56%) | — | 3 (7.89%) | 4 (3.45%) |
| Early Terminate, due to Adverse Event(s) | — | — | — | — |
| Early Terminate, for Other Reasons | 8 (20.51%) | 7 (17.95%) | 6 (15.78%) | 21 (18.1%) |
| Completed Study | 30 (76.92%) | 32 (82.05%) | 29 (76.32%) | 91 (78.4%) |
| Total | 39 (100.0%) | 39 (100.0%) | 38 (100.0%) | 116 (100.0%) |
| p Value | $\chi^2$ = 3.216, p = 0.522 | | | |

While the active HCA group had less non-completers than the placebo group (7 vs 9, respectively), these differences are not statistically significant. The Active formula had the same number of non-completers as the placebo group (9 vs 9).

The per-protocol population consists of 91 subjects (78.4%) who were randomized into three arms (30-Active formula Vs 32-Active HCA Vs 29-Placebo)

7.3.2 Baseline and Demographic Characteristics of the Subjects

As a check on the even randomization of subjects, the demographic, safety and efficacy variables were compared between the Active formula, Active HCA and placebo groups. Table 18 summarizes the characteristics of the subjects at baseline (defined as the average of the values at the screening and randomization visits).

Numeric variables are summarized in the format:
Mean±Standard Deviation
Median (Minimum–Maximum)

Categorical variables are shown as counts and percentages of total within product group. P-values in the last column of the table indicated whether there is a significant difference between the active and placebo groups as calculated by ANOVA. Nominally significant p-values (p<0.05) are highlighted in bold text.

TABLE 18

Baseline and Demographic Characteristics of Subjects (Completed Subjects)

| Variable | Active formula (n = 30) | Active HCA (n = 32) | Placebo (n = 29) | p-value |
|---|---|---|---|---|
| Demographic Variables | | | | |
| Age in years | 36.73 ± 8.34 37 (19-55) | 37.59 ± 7.92 38 (20-50) | 34.66 ± 8.41 33 (20-58) | 0.321 |

TABLE 18-continued

Baseline and Demographic Characteristics of Subjects (Completed Subjects)

| Variable | Active formula (n = 30) | Active HCA (n = 32) | Placebo (n = 29) | p-value |
|---|---|---|---|---|
| Gender | | | | |
| Female | 8 (26.6%) | 10 (31.3%) | 13 (44.8%) | 0.310 |
| Male | 22 (73.3%) | 22 (68.7%) | 16 (55.2%) | |
| Ethnicity | | | | |
| White | — | — | — | — |
| Black | — | — | — | — |
| Asian | 30 (100.0%) | 32 (100.0%) | 29 (100.0%) | — |
| American Indian | — | — | — | — |
| Others | — | — | — | — |
| Exercise at work | | | | |
| Sedentary | 7 (23.3%) | 6 (18.8%) | 10 (34.5%) | |
| Light | 18 (60.0%) | 14 (43.8%) | 10 (34.5%) | 0.272 |
| Moderate | 5 (16.7%) | 10 (31.3%) | 9 (31.0%) | |
| Heavy | — | 2 (6.3%) | — | |
| Physical Examination and Vital Signs | | | | |
| Height (m) | 1.59 ± 0.09 | 1.59 ± 0.08 | 1.62 ± 0.08 | 0.303 |
| | 1.58 (1.46-1.80) | 1.60 (1.45-1.75) | 1.63 (1.48-1.78) | |
| BMI (Kg/m$^2$) | 32.88 ± 2.73 | 32.77 ± 2.83 | 33.23 ± 3.81 | 0.157 |
| | 32.39 (28.5-8.75) | 32.93 (27.7-38.8) | 32.9 (28.02-38.65) | |
| HR (beats/min) | 79.10 ± 9.27 | 79.09 ± 10.68 | 80.28 ± 8.34 | 0.860 |
| | 76 (66-104) | 78 (59-100) | 80 (66-100) | |
| Systolic BP mm Hg | 123.87 ± 13.77 | 122.19 ± 12.63 | 123.26 ± 11.81 | 0.871 |
| | 120 (95-154) | 120 (104-160) | 120 (106-160) | |
| Diastolic BP mm Hg | 83.63 ± 8.87 | 83.00 ± 9.91 | 80.34 ± 9.29 | 0.365 |
| | 80 (69-100) | 80 (60-100) | 80 (65-100) | |
| ECG | | | | |
| Normal | 30 (100%) | 32 (100%) | 29 (100%) | |
| Abnormal | — | — | — | |
| Safety laboratory values | | | | |
| Hematocrit | 39.71 ± 3.69 | 39.24 ± 3.71 | 40.45 ± 3.64 | 0.442 |
| | 38 (34.1-47.2) | 39.2 (31.5-46.6) | 40 (34.50-51.30) | |
| Hemoglobin | 13.07 ± 2.02 | 13.14 ± 1.74 | 13.80 ± 2.01 | 0.279 |
| | 12.4 (10.7-17.1) | 13.5 (9.9-16.8) | 13.8 (11.20-18.4) | |
| Na | 141.07 ± 3.20 | 141.81 ± 2.78 | 140.21 ± 3.74 | 0.162 |
| | 142 (127-145) | 142 (135-149) | 140 (130-148) | |
| K | 4.53 ± 0.38 | 4.51 ± 0.39 | 4.55 ± 0.36 | 0.920 |
| | 4.5 (3.8-5.3) | 4.6 (3.70-5.30) | 4.5 (4.0-5.40) | |
| Cl | 105.30 ± 7.32 | 105.72 ± 4.39 | 106.14 ± 4.43 | 0.845 |
| | 101.5 (99-135) | 105.5 (100-113) | 107.0 (98-113) | |
| Creatinine | 0.87 ± 0.17 | 0.87 ± 0.19 | 0.89 ± 0.21 | 0.949 |
| | 0.9 (0.4-1.1) | 0.9 (0.50-1.20) | 0.9 (0.4-1.30) | |
| BUN | 17.44 ± 5.22 | 17.48 ± 3.87 | 18.34 ± 7.19 | 0.778 |
| | 16.5 (6.28-32) | 17.5 (9.30-26.0) | 16 (10.0-36.0) | |
| Ca | 9.01 ± 0.35 | 9.25 ± 1.46 | 9.03 ± 0.49 | 0.460 |
| | 9.1 (8.2-9.6) | 9.1 (8.10-17.0) | 9.0 (8.10-10.00) | |
| AST | 27.87 ± 10.69 | 27.41 ± 6.76 | 28.17 ± 6.98 | 0.936 |
| | 27 (12-69) | 27 (17-40) | 29 (12-43) | |
| ALT | 31.42 ± 12.30 | 34.72 ± 12.14 | 42.07 ± 17.16 | 0.016 |
| | 28 (19-63) | 32 (17-71) | 38 (17-82) | |
| Alk Phos | 95.63 ± 21.91 | 95.41 ± 21.02 | 90.45 ± 19.03 | 0.555 |
| | 101.5 (48-152) | 100.0 (45-123) | 96 (52-122) | |
| Total Bilirubin | 0.43 ± 0.32 | 0.36 ± 0.25 | 0.67 ± 0.65 | 0.018 |
| | 0.23 (0.1-1.0) | 0.21 (0.1-1.20) | 0.6 (0.10-3.20) | |
| Uric acid | 4.78 ± 0.91 | 4.62 ± 1.06 | 5.10 ± 1.36 | 0.241 |
| | 4.45 (3.8-7.3) | 4.3 (3.3-7.6) | 4.8 (1.8-8.3) | |
| TSH | 1.72 ± 1.33 | 2.18 ± 1.47 | 2.19 ± 1.24 | 0.299 |
| | 1.60 (0.15-5.53) | 1.78 (0.3-6.4) | 1.78 (0.3-5.2) | |
| Amylase | 45.21 ± 13.17 | 45.31 ± 15.09 | 45.79 ± 14.69 | 0.986 |
| | 42 (30-81) | 41.5 (30-89) | 42 (23-87) | |
| WBC | 8993.33 ± 1364.81 | 9034.38 ± 1580.45 | 8951.72 ± 1452.98 | 0.976 |
| | 8900 (6800-13200) | 8500 (7000-13700) | 8800 (5900-13100) | |
| Primary Efficacy Variables | | | | |
| Weight Kg | 84.20 ± 11.64 | 83.07 ± 10.92 | 87.63 ± 12.14 | 0.285 |
| | 83.37 (68.8-106.9) | 82.38 (66.57-112.0) | 85.46 (68.10-109.8) | |

TABLE 18-continued

Baseline and Demographic Characteristics of Subjects (Completed Subjects)

| Variable | Active formula (n = 30) | Active HCA (n = 32) | Placebo (n = 29) | p-value |
|---|---|---|---|---|
| Fat Mass In Gms | 32810.37 ± 7024.79 32364.5 (19908.0-46185.0) | 30942.46 ± 5916.88 31180.35 (16682.5-42065.5) | 33399.41 ± 8457.21 33355.9 (17978.0-47647.30) | 0.376 |
| Secondary Efficacy Variables | | | | |
| Lean Mass In Gms | 46388.46 ± 9334.98 43496.6 (33651.0-62982) | 47389.06 ± 10755.03 44565.5 (30390-69278.10) | 49707.05 ± 8748.72 50189.40 (38870.0-67210.0) | 0.407 |
| Bone Density | 1.144 ± 0.102 1.15 (0.985-1.307) | 1.154 ± 0.119 1.17 (0.934-1.382) | 1.205 ± 0.143 1.18 (0.956-1.597) | 0.133 |
| Abdominal girth | 98.90 ± 13.40 99.75 (72.5-130) | 99.28 ± 12.17 99.75 (81.0-127.0) | 100.50 ± 13.39 99.0 (75.50-129.0) | 0.945 |
| Total cholestrol | 181.97 ± 25.64 183 (117-256) | 172.00 ± 29.52 177 (108-221) | 183.93 ± 30.68 183 (126-249) | 0.220 |
| Triglycerides | 155.30 ± 40.42 145 (82-269) | 155.25 ± 45.19 146.5 (69-274) | 164.41 ± 62.39 143 (59-319) | 0.719 |
| LDL | 112.33 ± 18.87 108.5 (67-161) | 103.94 ± 25.71 106 (51-168) | 113.07 ± 26.77 109 (78-170) | 0.256 |
| VLDL | 30.78 ± 8.03 28.5 (16.4-53.8) | 30.95 ± 9.05 29.1 (13.80-54.80) | 32.71 ± 12.47 32.0 (11.80-63.80) | 0.713 |
| HDL | 38.30 ± 7.06 41.5 (21-48) | 35.93 ± 8.14 40.0 (15.0-44.0) | 37.83 ± 6.16 41.0 (26.0-46.0) | 0.395 |
| Blood Glucose | 83.90 ± 19.38 85.5 (70-124) | 87.09 ± 8.22 85.0 (70-106) | 87.72 ± 10.51 87.0 (70-113) | 0.909 |
| Insulin | 19.47 ± 9.59 17.50 (6.8-45) | 19.19 ± 10.53 17.25 (6.20-47.0) | 19.86 ± 13.74 15.70 (4.40-54.0) | 0.974 |
| HOMA-IR | 4.22 ± 2.21 3.83 (1.39-10.98) | 4.15 ± 2.37 3.61 (1.25-11.11) | 4.26 ± 3.03 3.18 (1.00-13.04) | 0.987 |
| Appetite (VAS-score) | 7.47 ± 3.87 7.10 (1-12) | 8.20 ± 4.05 8.80 (0-12) | 8.94 ± 3.98 12.20 (1-12) | 0.370 |
| Quality of life score (Total) | 34.50 ± 16.94 36.0 (2-72) | 35.22 ± 25.55 35.0 (0-76) | 32.41 ± 22.86 35.0 (0-74) | 0.879 |

7.3.3 Interpretation

Since no product had been administered at either of the baseline evaluations, we would expect baseline subject characteristics to be similar between groups, and this is generally what was found.

The only significant differences between product groups were slightly lower ALT and Total Bilirubin in the active groups compared to the placebo Group (Active formula ALT 31.42 U/L and Total Bilirubin 0.43 mg/dL, Active HCA ALT 34.72 U/L and Total Bilirubin 0.36 mg/dL, Placebo ALT 42.07 U/L and Total Bilirubin 0.67 mg/dL, p=0.016 and 0.018 respectively). This difference may be due to random fluctuations—2 differences would not be an unexpected occurrence in 41 significant tests.

Active groups had a lower body weight (Active Formula 84.20 kg, Active HCA 83.07 Kg and Placebo 87.63 Kg), but the difference was not statistically significant (P=0.285).

7.4 Safety Analysis 7.4.1 Adverse Events

No serious adverse events were noted in this study.

Table 19 lists each of the adverse events reported during this study for completed subjects. Tables 20, 21, and 22 list the severity and probable relationship to each group of each adverse event.

TABLE 19

Adverse Events Reported by Each Group for Completed Subjects

| ADVERSE EVENTS | Active formula | Active HCA | Placebo | Total |
|---|---|---|---|---|
| Constipation | | | 1 | 1 |
| Headache earlier | | | 1 | 1 |
| Ankle and foot pain | | | 1 | 1 |
| Back pain | 1 | 1 | | 2 |
| Boils on his legs due to heat | | | 1 | 1 |
| Constipation | | 1 | | 1 |
| Dry cough, severe cold and nose block | | 1 | | 1 |
| Dryness of mouth | | | 1 | 1 |
| Fever for 2 days | | 1 | | 1 |
| Gastric problem | | | 1 | 1 |
| Gastritis | | 1 | | 1 |
| Gastritis, back pain | 1 | | | 1 |
| Increased appetite | | 1 | | 1 |
| Irregular periods | | | 1 | 1 |
| Irritation in the chest | | 1 | | 1 |
| Joint pain, gastritis | | | 1 | 1 |
| Knee pain | | | 1 | 1 |
| Leg and back pain | 1 | | | 1 |
| Leg pain | 1 | | 1 | 2 |
| Leg pain, giddiness | 1 | | | 1 |
| Loose motion | | 2 | | 2 |
| Loose motion and stomach upset | | | 1 | 1 |
| Neck pain | 1 | | | 1 |
| Palpitation 5-10 minutes every day in the morning | 1 | | | 1 |
| Skin irritation, asthma | 1 | | | 1 |
| Tiredness | 1 | | 1 | 2 |
| Tiredness, headache, giddiness | | | 2 | 2 |
| Tiredness, tension, gastritis | | 1 | | 1 |
| Weakness | | | 1 | 1 |

TABLE 20

Adverse Events, by Product Group-Active Formula

| Sl. No | Sub No | Event Description | Severity | Relationship |
|---|---|---|---|---|
| 1 | 49 | Leg and back pain | Mild | Unrelated |
| 2 | 6 | Tiredness | Mild | Probable |
| 3 | 13 | Gastritis, back pain | Severe | Certain |
| 4 | 39 | Neck pain | Moderate | Unrelated |
| 5 | 40 | Skin irritation, asthma | Severe | Unrelated |
| 6 | 41 | Back pain | Moderate | Probable |
| 7 | 87 | Palpitation 5-10 minutes every day in the morning and constipation | Mild | Certain |
| 8 | 97 | Leg pain | Moderate | Probable |
| 9 | 111 | Leg pain, giddiness | Mild | Probable |

TABLE 21

Adverse Events, by Product Group-Active HCA

| Sl. No | Sub No | Event Description | Severity | Relationship |
|---|---|---|---|---|
| 1 | 48 | Irritation in the chest | Moderate | Probable |
| 2 | 50 | Gastritis | Moderate | Probable |
| 3 | 12 | Fever for 2 days | Moderate | Unrelated |
| 4 | 14 | Loose motion | Moderate | Unrelated |
| 5 | 16 | Loose motion | Moderate | Unrelated |
| 6 | 42 | Back pain | Moderate | Probable |
| 7 | 47 | Tiredness, tension, gastritis | Severe | Probable |
| 8 | 44 | Dry cough, severe cold and nose block | Severe | Unrelated |
| 9 | 110 | Constipation | Severe | Probable |
| 10 | 83 | Increased appetite | Moderate | Probable |

TABLE 22

Adverse Events, by Product Group-Placebo

| Sl. No | Sub No | Event Description | Severity | Relationship |
|---|---|---|---|---|
| 1 | 8 | Weakness | Moderate | Unrelated |
| 2 | 7 | Irregular periods | Moderate | Unrelated |
| 3 | 37 | Dryness of mouth | Moderate | Probable |
| 4 | 46 | Ankle and foot pain | Severe | Unrelated |
| 5 | 86 | Tiredness | Mild | Probable |
| 6 | 53 | Knee pain | Very Severe | Probable |
| 7 | 80 | Joint pain, gastritis | Moderate | Probable |
| 8 | 89 | Gastric problem | Moderate | Probable |
| 9 | 98 | Leg pain | Moderate | Probable |
| 10 | 74 | Constipation | Moderate | Probable |
| 11 | 77 | Tiredness, headache, giddiness | Mild | Probable |
| 12 | 78 | Tiredness, headache, giddiness | Mild | Probable |
| 13 | 75 | Loose motion and stomach upset | Moderate | Probable |
| 14 | 76 | Headache earlier | Moderate | Unrelated |
| 15 | 85 | Boils on his legs due to heat | Severe | Probable |

A total of 34 adverse events were experienced by the subjects in the per protocol population. Of this, the placebo group reported 15 adverse events. The Active formula group reported 9 adverse events and the Active HCA group reported 10 adverse events. There was no significance between the three groups (p=0.193) nor was there significance when comparing the Active formula group with placebo (p=0.089) and Active HCA with placebo (p=0.179).

Even though there was no significant difference between the three groups, a general trend was observed whereby the adverse events can be grouped into two main categories—joint pain and gastritis. However, these events appeared across all three groups and could not be attributed to any one group.

Adverse events were not responsible for any early terminations for any of the subjects for any of the groups.

7.4.2 Safety Laboratory Values and Vital Signs

Tables 23, 24, 25, and 26 summarize the change in safety lab values from baseline to end of study (week 12) for each product group. Baseline is defined as the average of available values from the screening and/or randomization visit (prior to dispensation of study product).

Variables are summarized in the format:

Mean±Standard Deviation

For the tables corresponding to Physical examination and vital signs the significance data is represented at the bottom most row of the tables—this has been calculated by repeated measures ANOVA. For the tables corresponding to safety lab values non-identical superscripts are significant at p<0.05, identical superscripts are not significant using the Student t test with Bonferroni correction.

This summary is based on the completed subjects.

TABLE 23

Hemodynamics (Pulse Rate)

| Time Period | Active formula (n = 30) | Active HCA (n = 32) | Placebo (n = 29) |
|---|---|---|---|
| Baseline | 79.10 ± 9.27 | 79.09 ± 10.68 | 80.28 ± 8.35 |
| At 2 weeks | 77.27 ± 10.80 | 77.75 ± 10.06 | 78.76 ± 9.03 |
| At 4 weeks | 77.37 ± 10.93 | 80.44 ± 8.36 | 79.32 ± 9.81 |
| At 6 weeks | 76.80 ± 7.85 | 76.75 ± 7.91 | 77.52 ± 7.51 |
| At 8 weeks | 76.33 ± 8.21 | 76.28 ± 10.89 | 77.75 ± 10.05 |
| At 10 weeks | 76.17 ± 8.29 | 76.78 ± 8.85 | 75.97 ± 8.66 |
| At 12 weeks | 75.20 ± 7.22 | 74.06 ± 7.93 | 74.76 ± 6.25 |
| Significance by Repeated Measures ANOVA | p = 0.582 | p = 0.031 | p = 0.115 |

TABLE 24

Hemodynamics (Systolic Blood Pressure)

| Time Period | Active formula (n = 30) | Active HCA (n = 32) | Placebo (n = 29) |
|---|---|---|---|
| Baseline | 123.87 ± 13.77 | 122.19 ± 12.64 | 123.28 ± 11.81 |
| At 2 weeks | 121.97 ± 10.89 | 122.56 ± 10.56 | 122.38 ± 12.01 |
| At 4 weeks | 122.27 ± 11.41 | 121.13 ± 10.05 | 124.04 ± 12.82 |
| At 6 weeks | 119.30 ± 12.15 | 118.63 ± 12.32 | 119.41 ± 11.66 |
| At 8 weeks | 118.43 ± 11.05 | 118.66 ± 12.79 | 121.71 ± 9.06 |
| At 10 weeks | 118.80 ± 9.41 | 118.56 ± 12.06 | 120.00 ± 11.51 |
| At 12 weeks | 122.53 ± 12.83 | 117.97 ± 9.23 | 120.45 ± 12.05 |
| Significance by Repeated Measures ANOVA | p = 0.125 | p = 0.302 | p = 0.158 |

TABLE 25

Hemodynamics (Diastolic Blood Pressure)

| Time Period | Active formula (n = 30) | Active HCA (n = 32) | Placebo (n = 29) |
|---|---|---|---|
| Baseline | 83.63 ± 8.86 | 83.00 ± 9.91 | 80.34 ± 9.29 |
| At 2 weeks | 78.73 ± 9.68 | 79.88 ± 7.62 | 80.28 ± 10.94 |
| At 4 weeks | 83.13 ± 9.41 | 79.06 ± 9.19 | 81.79 ± 8.49 |
| At 6 weeks | 79.87 ± 9.83 | 79.22 ± 9.85 | 79.24 ± 9.25 |
| At 8 weeks | 78.00 ± 9.63 | 78.31 ± 10.16 | 79.11 ± 8.49 |
| At 10 weeks | 78.27 ± 8.58 | 78.31 ± 10.16 | 78.41 ± 7.82 |
| At 12 weeks | 79.63 ± 9.81 | 77.00 ± 6.85 | 78.41 ± 10.64 |
| Significance by Repeated Measures ANOVA | p = 0.012 | p = 0.016 | p = 0.755 |

TABLE 26

Safety Lab Values

| Variable/time period | | Active formula (n = 30) | Active HCA (n = 32) | Placebo (n = 29) |
|---|---|---|---|---|
| Hematocrit | Baseline | 39.71 ± 3.69$^a$ | 39.24 ± 3.71$^a$ | 40.45 ± 3.64$^a$ |
| | At 12 weeks | 40.88 ± 4.01$^b$ | 40.33 ± 3.60$^a$ | 41.84 ± 4.02$^a$ |
| FBS | Baseline | 83.90 ± 19.38$^a$ | 87.09 ± 8.22$^a$ | 87.72 ± 10.51$^a$ |
| | At 12 weeks | 86.27 ± 7.79$^a$ | 83.94 ± 7.81$^a$ | 85.17 ± 8.22$^a$ |
| Insulin | Baseline | 19.47 ± 9.59$^a$ | 19.19 ± 10.53$^a$ | 19.86 ± 13.74$^a$ |
| | At 12 weeks | 21.73 ± 12.31$^a$ | 21.07 ± 12.04$^a$ | 28.17 ± 17.99$^b$ |
| Bone Density | Baseline | 1.144 ± 0.102$^a$ | 1.154 ± 0.119$^a$ | 1.205 ± 0.143$^a$ |
| | At 12 weeks | 1.154 ± 0.087$^a$ | 1.151 ± 0.111$^a$ | 1.203 ± 0.131$^a$ |
| HOMA-IR | Baseline | 4.22 ± 2.21$^a$ | 4.15 ± 2.37$^a$ | 4.26 ± 3.03$^a$ |
| | At 12 weeks | 4.71 ± 2.79$^a$ | 4.18 ± 2.59$^a$ | 5.85 ± 3.60$^b$ |
| Hemoglobin | Baseline | 13.07 ± 2.02$^a$ | 13.14 ± 1.74$^a$ | 13.80 ± 2.01$^a$ |
| | At 12 weeks | 13.24 ± 1.94$^a$ | 13.09 ± 1.68$^a$ | 13.67 ± 2.01$^a$ |
| WBC | Baseline | 8993.33 ± 1364.81$^a$ | 9034.38 ± 1580.45$^a$ | 8951.72 ± 1452.98$^a$ |
| | At 12 weeks | 8590.00 ± 1176.01$^a$ | 8125.81 ± 855.17$^b$ | 8803.45 ± 1868.82$^a$ |
| Na | Baseline | 141.07 ± 3.20$^a$ | 141.81 ± 2.78$^a$ | 140.21 ± 3.74$^a$ |
| | At 12 weeks | 138.87 ± 2.32$^b$ | 139.26 ± 2.76$^b$ | 140.00 ± 2.66$^a$ |
| K | Baseline | 4.53 ± 0.38$^a$ | 4.51 ± 0.39$^a$ | 4.55 ± 0.36$^a$ |
| | At 12 weeks | 4.48 ± 0.27$^a$ | 4.43 ± 0.38$^a$ | 4.53 ± 0.35$^a$ |
| Cl | Baseline | 105.30 ± 7.32$^a$ | 105.72 ± 4.39$^a$ | 106.14 ± 4.43$^a$ |
| | At 12 weeks | 104.53 ± 4.04$^a$ | 104.45 ± 3.92$^a$ | 104.28 ± 3.37$^b$ |
| Creatinine | Baseline | 0.87 ± 0.17$^a$ | 0.87 ± 0.19$^a$ | 0.89 ± 0.21$^a$ |
| | At 12 weeks | 0.89 ± 0.16$^a$ | 0.84 ± 0.19$^a$ | 0.93 ± 0.17$^a$ |
| BUN | Baseline | 17.44 ± 5.22$^a$ | 17.48 ± 3.87$^a$ | 18.34 ± 7.19$^a$ |
| | At 12 weeks | 16.73 ± 3.52$^a$ | 17.05 ± 4.16$^a$ | 16.14 ± 4.49$^a$ |
| AST | Baseline | 27.87 ± 10.69$^a$ | 27.41 ± 6.76$^a$ | 28.17 ± 6.98$^a$ |
| | At 12 weeks | 24.40 ± 6.45$^a$ | 23.29 ± 7.26$^b$ | 25.07 ± 7.29$^a$ |
| ALT | Baseline | 31.42 ± 12.30$^a$ | 34.72 ± 12.14$^a$ | 42.07 ± 17.16$^a$ |
| | At 12 weeks | 30.71 ± 12.74$^a$ | 31.61 ± 11.29$^a$ | 39.00 ± 17.41$^a$ |
| Alk Phos | Baseline | 95.63 ± 21.91$^a$ | 95.41 ± 21.02$^a$ | 90.45 ± 19.03$^a$ |
| | At 12 weeks | 95.06 ± 16.94$^a$ | 93.58 ± 17.29$^a$ | 93.03 ± 18.18$^a$ |
| Total Bilirubin | Baseline | 0.43 ± 0.32$^a$ | 0.36 ± 0.25$^a$ | 0.67 ± 0.65$^a$ |
| | At 12 weeks | 0.38 ± 0.30$^a$ | 0.34 ± 0.24$^a$ | 0.60 ± 0.47$^a$ |
| Uric Acid | Baseline | 4.78 ± 0.91$^a$ | 4.62 ± 1.06$^a$ | 5.10 ± 1.36$^a$ |
| | At 12 weeks | 4.76 ± 1.11$^a$ | 4.56 ± 1.04$^a$ | 4.89 ± 1.40$^a$ |
| TSH | Baseline | 1.72 ± 1.33$^a$ | 2.18 ± 1.47$^a$ | 2.19 ± 1.24$^a$ |
| | At 12 weeks | 1.65 ± 0.83$^a$ | 1.92 ± 0.76$^a$ | 1.94 ± 0.84$^a$ |
| Amalyse | Baseline | 45.21 ± 13.17$^a$ | 45.31 ± 15.09$^a$ | 45.79 ± 14.69$^a$ |
| | At 12 weeks | 43.72 ± 15.48$^a$ | 46.13 ± 19.54$^a$ | 45.55 ± 16.22$^a$ |

Three of the physical examination variables underwent statistically significant changes from baseline to end of study:
  a. 3.9 beats/min decrease in pulse rate in active formula group
  b. 4 mm Hg decrease in Diastolic Blood Pressure in active Formula group
  c. 6 mm Hg decrease in Diastolic Blood Pressure in active. HCA group The change observed in the pulse rate was not clinically significant as the mean values are within the normal range for all three groups at the end of the study. Even though there was a significant decrease in the pulse rate of the active HCA this can be attributed to random fluctuations. From a safety perspective, there were no clinically significant changes in the diastolic blood pressure in the active formula group and the active HCA group.

Furthermore; the comparison between the above variables to the corresponding placebo variables were not statistically significant.

Eight of the safety laboratory variables underwent statistically significant changes from baseline to end of study:
  a. 2.2 mEq/L decrease in Na in active formula group
  b. 2.55 mEq/L decrease in Na in active HCA group
  c. 1.86 mEq/L decrease in Cl in placebo group
  d. 4.12 U/L decrease in AST in active HCA group
  e. 1.17% increase in Hematocrit in active formula group
  f. 8.31 μu/ml increase in Insulin in placebo group
  g. 1.59 increase in HOMA-IR in placebo group
  h. 908.57 thousands/μl decrease in WBC in Active HCA group When comparing the above variables to the corresponding placebo variables it was found that there was no statistical significance for Na, Cl, Hematocrit, or AST. However, the active HCA group showed a significant decrease in WBC.

From a safety perspective the changes observed were not clinically significant as the mean values for the Na, Cl, AST and WBC are within the normal range for all three groups at the end of the study. The increase in Hemocrit in the active formula group can be attributed to intra-inter observer variability and therefore is also not clinically significant from a safety perspective.

The increase in Insulin and the consequent increase in HOMA-IR in the placebo group can be attributed to a few outliers in the placebo group. Three outliers have been identified and their details are as follows:
  a. Subject No. 54 had a baseline Insulin value of 31 μu/ml and an end of study insulin value of 66 μu/ml
  b. Subject No. 89 had a baseline Insulin value of 14.2 μu/ml and an end of study insulin value of 49.2 μu/ml
  c. Subject No. 113 had a baseline Insulin value of 20 μu/ml and an end of study insulin value of 46 μu/ml If these outliers are dropped then the insulin and HOMA-IR increases will also become insignificant for the placebo group.

7.4.3 Safety Conclusions

Four safety values showed nominally significant average changes from baseline to end of study in the active formula group (Decrease in Pulse, Diastolic blood pressure, Na, and an increase in Hematocrit).

Four safety values showed nominally significant average changes from baseline to end of study in the active HCA group (Decrease in Diastolic blood pressure, AST, Na and WBC).

Three safety values showed nominally significant average changes from baseline to end of study in the placebo group (increase in Insulin and HOMA-IR and a decrease in CI).

There were no significant differences between the Active groups and placebo for all variables except WBC. The Active HCA group did show a decrease in WBC as compared to placebo. However, this change was not of a clinically important magnitude.

Generally, this study provided no reason for safety concerns.

7.4.4 Efficacy Analysis

In addition, the active formula group and active HCA groups also showed a significant reduction in abdominal girth which was listed as a secondary efficacy objective.

Furthermore, the both active groups also showed a decrease in diastolic blood pressure and AST broadly indicating an improving metabolic profile.

7.5 Compliance

Compliance was analyzed from baseline to the end of study and for, every two week period as well. Percentage compliance for the total and 2 week time period (Baseline to end of study) was calculated in the following manner:

a. The number of pills returned was divided by the total pills dispensed during the corresponding period.
b. The above number was then subtracted from the number 1 and the resulting number was multiplied by 100.

Table 27 summarizes these compliance measures and compares them between product groups. Numerical data is presented in the format:

Mean±Standard Deviation

TABLE 27

Compliance (%) by Product (from Returned-Product Count)

| Study period | Active formula (n = 30) | Active HCA (n = 32) | Placebo (n = 29) |
|---|---|---|---|
| Week2 | 84.53 ± 17.71 | 84.11 ± 10.64 | 85.68 ± 16.45 |
| Week4 | 84.44 ± 17.57 | 86.02 ± 8.27 | 88.36 ± 10.97 |
| Week6 | 79.39 ± 22.49 | 84.67 ± 11.97 | 89.60 ± 10.92 |
| Week8 | 90.74 ± 7.34 | 88.88 ± 8.86 | 89.89 ± 9.71 |
| Week10 | 87.22 ± 10.17 | 85.89 ± 16.99 | 94.06 ± 6.85 |
| Week12 | 90.16 ± 15.85 | 90.75 ± 11.33 | 88.50 ± 21.04 |
| Baseline to end of study | 86.08 ± 6.10 | 86.72 ± 5.88 | 89.35 ± 7.60 |

All the three groups had a high level of compliance on a 2 week basis. This was also observed when considering the baseline to end-of-study time period.

Overall, compliance was very good and adequate for the purposes of this study.

7.6 Additional Information about the Study

This section describes the design of the study, the data management methods, the parameters studied, and the statistical methods used. It presents results in the form of summary tables and graphs with significance levels, effect size and interpretations.

7.6.1 Description of the Study Design
7.6.1.1 Purpose, Objective and Endpoints of the Study The Purpose of this study is to test the Efficacy and Safety of two experimental Weight loss products as compared to placebo over a 12-week period in healthy overweight and obese adults.

The Specific objectives and corresponding endpoints are summarized here. All effects that are defined as 12 week changes from baseline to end of the study. All Efficacy and Safety objectives involve comparing the active supplements to placebo, with regard to each of the following endpoints.

Primary Efficacy Endpoints

Reduced fat mass on the dual energy x-ray absorptiometry (DEXA) scan between baseline and 12 week visit and loss of 5% or more of body weight at 12 weeks Secondary Efficacy Endpoints Improved body composition, increase lean mass and improved bone density measured by dual energy x-ray absorptiometry (DEXA) scan
Reduced abdominal girth
Improved lipid Profiles
Reduced Insulin resistance calculated by the HOMA-IR method.
Ability to maintain a weight loss diet and/or diminished appetite.
Improved quality of Life based on a Quality of life questionnaire (QLQ)

Primary Safety Endpoints

Physical Examination (HR, SBP, DBP)
Safety laboratory values (Complete Blood count (CBC), BUN, electrolytes, glucose, creatinine, calcium, AST, ALT, Alkaline Phosphatase, total bilirubin, uric acid, urine analysis, cholesterol, triglycerides, TSH, IIbA1c, pregnancy test (females), amylase)

Secondary Safety Parameters

Adverse Events

7.6.1.2 Structure of the Study

This is a three-group, prospective, parallel, randomized, double blind placebo-controlled clinical trial.

7.6.1.3 Description of the Study

The study enrolled healthy adult males and females in the age group 18 to 60 years, who had BMI values between 28 and 40 kg/m$^2$.

All, the subjects were pre-screened at site visits; Potential candidates were called in for a screening and baseline evaluation after obtaining informed consent. Acceptable subjects were enrolled and randomized for the three arms (1:1:1 ratio) to receive active formula, active HCA or placebo for 12 weeks. As per the protocol, efficacy and safety evaluations were performed at baseline, week 2, week 4, week 6, week 8, week 10 and week 12.

The respective IRB/Ethics committees of the centres where the study was carried out approved this study: 1. St. Johns Medical College Hospital, Bangalore, India, and 2. M.S. Ramiah Medical College Hospital, Bangalore, India.

7.6.1.4 Testing Protocol

Table 28 summarizes the activities performed at each visit of the study. A complete description of each visit's activities is provided in the protocol.

TABLE 28

Activities Performed at Each Visit

| | Screening Week −1 | Baseline Week 0 | Week +2 | Week +4 | Week +6 | Week +8 | Week +10 | Week +12 |
|---|---|---|---|---|---|---|---|---|
| Consent | x | | | | | | | |
| Demographics | x | | | | | | | |
| Exclusion/Inclusion | x | x | | | | | | |
| History/concomitant medication | x | | | | | | | |
| Physical Exam | x | | | | | | | x |
| EKG | x | | | | | | | x |
| Dietician instructions | | x | | | | | | |
| Weight, girth, BMI, BP, pulse | (BMI) | x | x | x | x | x | x | x |
| DEXA | | x | | | | | | x |
| Routine lab[1] | x | | | | | | | x |
| Lipid profile | x | | | | | | | x |
| Insulin/glucose | x | | | | | | | x |
| Appetite/satiety VAS | | x | | | x | | | |
| Quality of life (QOL) | | x | | | | | | x |
| Exercise level | | x | x | x | x | x | x | x |
| Diary review/compliance | | | x | x | x | x | x | x |
| Adverse events/concomitant medications | | | x | x | x | x | x | x |
| Pill counts | | | x | x | x | x | x | x |
| Dispense study compound | | x | x | x | x | x | x | |

[1]Complete Blood count (CBC), BUN, electrolytes, glucose, creatinine, calcium, AST, ALT, Alkaline Phosphatase, total bilirubin, uric acid, urine analysis, cholesterol, triglycerides, TSH, HbA1c, pregnancy test (females), amylase.

Visits after the screening visit will have a window of +/−7 days

7.6.2 Data Management Methods

All data elements recorded during the study period were entered and validated by K. P. Suresh (Statistician) in Microsoft Excel. Definitions of the data elements entered are shown in Table 29. The randomization key was transmitted electronically by the vendor to the statistician and each subject's supplement product group assignment was transferred electronically into the data spreadsheet on the basis of the subjects' randomization numbers.

Body mass index was calculated from height and weight. All variables and changes were transferred into the SPSS, SYSTAT statistical software, summarized (Counts, Minimum, Maximum, Mean, Median, Standard Deviation) within each treatment group, transferred to the statistical report and then reformatted. Suitable graphs were generated to depict the changes in key efficacy parameters and then transferred to the statistical report.

7.6.3 Data Elements, Efficacy and Safety Parameters

TABLE 29

Data Elements

| Data Elements | Definition |
|---|---|
| Initial | Subject Initial |
| Code | Assigned Randomization number |
| Visit | Which visit the data was collected, per protocol |
| Gender | Male or Female |
| Age | Age in years |
| Race | Which Ethnicity the subject circled on the demographics or other related sheet |
| Height | Height in meters |
| Weight | Weight in kilograms |
| BMI | Weight in Kilograms/Height in Meters squared |
| Body fat | Total body fat as measured by DEXA in gms |
| Lean Mass | Total body lean mass as measured by DEXA in gms |
| Cholesterol | Total Cholesterol mg/dL |
| Triglycerides | Total Triglycerides mg/dL |

TABLE 29-continued

Data Elements

| Data Elements | Definition |
|---|---|
| LDL | Low Density Lipoprotein mg/dL |
| VLDL | Very Low Density Lipoprotein mg/dL |
| HDL | High Density Lipoprotein mg/dL |
| Glucose | Fasting Blood sugar mg/dL |
| Insulin | Fasting Insulin μu/ml |
| Hemocrit | Hemocrit level % |
| Hemoglobin | Hemoglobin level g/dL |
| White Cell Count | White Blood Cells Count thousands/micro liter |
| Creatinine | Creatinine level mg/dL |
| BUN | Blood Urea Nitrogen mg/dL |
| Na | Fasting Sodium-electrolyte value, mEq/L |
| K | Fasting Potassium electrolyte value, mEq/L |
| Cl | Fasting Chloride electrolyte value, mEq/L |
| Ca | Fasting Calcium, mg/dL |
| AST | Aspartate Amino Transaminase, U/L |
| ALT | Alanine Amino Transferase, U/L |
| Alk Phos | Alkaline Phosphatase, U/L |
| Total Bilirubin | Fasting Total Bilirubin, mg/dL |
| Uric Acid | Fasting Uric Acid, mg/dL |
| TSH | Thyroid Stimulating Hormone, μIu/ml |
| Amylase | Fasting Amylase, U/L |
| Kcal | Food intake at appetite test, Kcals |
| Appetite | Measured on visual analogue scale. 0-12.2 |
| Blood Pressure | Systolic/Diastolic blood pressure, mm Hg |
| Pulse | Resting pulse, beats/min |
| QOL | Weight Loss quality of life questionnaire |
| Symptom Measure | Weight related Symptom Measure |
| Compliance | % Compliance with taking assigned product |

7.6.4 Statistical Methods

7.6.4.1 Definition of Study Population

The per protocol population is defined as all enrolled subjects who completed all scheduled visits and an overall product compliance rate of at least 75%. Safety and efficacy analysis was performed on this population.

7.6.4.2 Descriptive Statistics

Descriptive statistics for each numerical variable was summarized as the mean and standard deviations for all the subjects at each time interval in each study group.

7.6.4.3 Changes Over Time

One-way Repeated Measures ANOVA assessed changes over time from baseline to each subsequent visit within each product group.

Pair wise significance with Bonferroni Correction assessed changes over two points (baseline to end of study) for each study group.

Treatment Effects were assessed by comparing the week-12 parameters between Active products and Placebo keeping the baseline values as covariates by the Analysis of Covariance (ANCOVA).

7.6.4.4 Adverse Events

All the adverse events/complications were recorded for every visit for each product and the obtained frequencies were tabulated and tested for significance with Placebo by Chi-square/Fisher Exact Test.

7.6.4.5 Control of Type-1 Error

All statistical tests were conducted at the 0.05 alpha level, meaning that $P \leq 0.05$ was considered "nominally significant". The Adjustment for multiple tests was made by applying Bonferroni correction to the p-values. The p-value for the comparison of the primary efficacy endpoints between active and placebo group was considered to be conclusive.

7.6.4.6 Software

The Statistical software namely SPSS 11.0 and Systat 8.0 were used for the analysis of the data and Microsoft word and Excel were used to generate graphs and tables.

The specification, examples and data provide a complete description of the manufacture and use of the composition of the invention. Since many embodiments of the invention can be made without departing from the spirit and scope of the invention, the invention resides in the claims hereinafter appended.

All publications and patent applications cited in this specification are indicative of the level of ordinary skill in the art to which this invention pertains and are incorporated herein by reference in their entireties.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention without following the example embodiments and applications illustrated and described herein, and without departing from the true spirit and scope of the present invention, which is set forth in the following claims.

REFERENCES CITED

| | | | |
|---|---|---|---|
| 3,764,692 | October 1973 | Lowenstein et al | 424/279 |
| 6,399,089 | April 2002 | Yegorova, et al | 424/439 |
| 6,784,206 | August 2004 | Udell, et al | 514/557 |
| 6,830,765 | December 2004 | Rombi | 424/729 |
| 2004/0259937 | April 2000 | Samuel et al | 514/460 |
| WO/2005/014020 | July 2005 | KROTKIEWSKI et al | |
| WO/2005/067952 | February 2005 | BAGCHI et al | |

Arion W J, et al. (1997) Chlorogenic Acid Analogue S 3483: A Potent Competitive Inhibitor of the Hepatic and Renal Glucose-6-Phosphatase Systems. Archives of Biochemistry and Biophysics; 339(2):315-322.

Hayamizu, K., Ishii Y., Knaeko, I., Shen, M., Okuhara, Y., Shigematsu, N., Tomi, H., Furuse, M., Yohsino, G., and Shimasaki, H.; (2003) Effects of *Garcinia cambogia* (Hydroxycitric acid) on Visceral fat accumulation: A double blind, randomized, placebo controlled trial, Curr Ther Res Clin Exp. 64: 551-567

Hemmerle H, et al. (1997) Chlorogenic acid and synthetic chlorogenic acid derivatives: novel inhibitors of hepatic glucose-6-phosphate translocase. Journal of Medicinal Chemistry 40(2):137-145.

Hertog, M. G., Kromhout, D., Aravanis, C., Blackburn, H., Buzina, R., Fidanza F, Giampaoli, S., Jansen, A., Menotti, A, Nedeljkovic, S., Pckkarinen, M., Simic, B. S., Toshima, H., Feskens, E. J. M., Hollman, P. C. H., Katan, M. P. (1995) Flavonoid intake and long-term-risk of coronary heart disease and cancer in the Seven Countries Study. Arch. Intern. Med., 155, 381-386 [abstract]

Heymsfield, S. B., Allison, D., Vasselli, J. Pietrobelli, A, Greenfield, D. and Nunez, C. (1998) *Garcinia cambogia* (Hydroxycitric Acid) as a Potential Antiobesity Agent: A Randomized Controlled Trial. JAMA: The Journal of the American Medical Association. 280(18): 1596-1600.

Heymsfield, S B, Allison, D B, Vasselli, J R, Pietrobelli, A, Greenfield, D, and Nunez, C. (1998) *Garcinia cambogia* (hydroxycitric acid) as a potential antiobesity agent: a randomized controlled trial. JAMA. 280, 1596-600.

Hollman, P. C. H., Feskens, E. J. M. & Katan, M. B. (1999) Tea flavonols in cardiovascular disease and cancer epidemiology. Proc. Soc. Exp. Biol. Med., 220, 198-202.

Ikeda Y et al. (1999) Effectiveness and safety of Banabamin tablets containing an extract from banaba in patients with mild type 2 diabetes. Japan Pharmacol Ther 27:67-73.

Johnston K L et al. Coffee acutely modifies gastrointeginal hormone secretion and glucose tolerance in humans: glycemic effects of chlorogenic acid and caffeine. Am J Clin Nutr. Oct; 78(4):728-33, 2003

Juneja L R, Chu D-C, Okubo T, et al. (1999) L-theanine a unique amino acid of green tea and its relaxation effect in humans. Trends Food Sci Tech. 10:199-204.

Knowler W C Barrett-Connor E Fowler S E, et al. (2002) Reduction in the incidence of type 2 diabetes with lifestyle intervention or Metformin. New England Journal of Medicine. 346:393-403

Loe Y C et al. (2001) Gas chromatography/mass spectrometry method to quantify blood hydroxycitrate concentration." Annal Biochem 292, 1:148-54.

Loe Y C et al. (2001) Time course of hydroxycitrate clearance in fasting and fed humans. FASEB J 15, 4:632, Abs. 501.1.

Mahendran, P., Shymala Devi, C. S. (2001) The Modulating effect of *Garcinia cambogia* extract on ethanol induced peroxidative damage in rats, Indian J of Pharmacology, 33: 87-91

Mason R. (2001) 200 mg of Zen; L-theanine boosts alpha waves, promotes alert relaxation. Alternative & Complementary Therapies, April; 7:91-9.

Murakami C et al. (1993) Screening of plant constituents for effect on glucose transport activity in Ehrlich ascites tumour cells. Chem and Pharm Bulletin (Tokyo) Dec; 41(12): 2129-31.

Nathan D M. (1993) Long-term complications of diabetes mellitus. New England Journal of Medicine, 328:1676-1685.

National Cholesterol Education Program Expert Panel on Detection, Evaluation, and Treatment of High Blood Cholesterol in Adults (Adult Treatment Panel III), NIH Publication No. 02-5215, September 2002.

Preuss H. G., D. Bagchi, C. V. S. Rao, B. W. Echard, S. Satyanarayana, and M. Bagchi (2002) Effect of hydroxycitric acid on weight loss, body mass index and plasma leptin levels in human subjects. FASEB J. 16(5):A 1020.

Preuss, H. G. (2004) Bagchi D., Bagchi, M., Rao, C. V. S, Satyanarayana, S., Dey, D. K. Efficacy of a novel, natural extract of (−)-hydroxycitric acid (HCA-SX) and a combination of HCA-SX, niacin-bound chromium and *Gymnema sylvestre* extract in weight management in human volunteers; A pilot study. Nutrition Research 24 45-58.

Schaefer B. Coffee consumption and type 2 diabetes mellitus [letter]. (2004) Ann Intern Med. 141:321

Shirai M. et al. (1994) Single Forced Oral Administration Toxicity Test on Mouse by Banaba Extract Jpn Pharmacol Ther, 22(11): 119 121.

Sullivan C., and Triscari J. (1977) Metabolic regulation as a control for lipid disorders. I. Influence of (−)-hydroxycitrate on experimentally induced obesity in the rodent. Am J Clin Nutr 30:767-76.

Suzuki Y et al. (1999) Antiobesity activity of extracts from *Lagerstroemia speciosa* L. leaves on female KK-Ay mice. J Nutr Sci Vitaminol (Tokyo) 45(6):79'-5.

Tommasi N D et al. (1991) Hypoglycemic effects of sesquiterpene glycosides and polyhydroxylated triterpenoids of Eriobotry japonica. Planta Medica 57: 414-416.

Tuomilehto J, Lindstrom J, Eriksson J G, et al. (2001) Prevention of type 2 diabetes mellitus by changes in lifestyle among subjects with impaired glucose tolerance. New England Journal of Medicine. 344:1343-1350.

van Dam, R. M. and F. B. Hu (2005) Coffee Consumption and Risk of Type 2 Diabetes A Systematic Review; J. Am. Med. Assoc. 294: 97 van Loon, Luc J C, Johannes J M van Rooijen, Bas. Niesen, Hans Verhagen, Wim H M Saris, and Anton J M (2000 Wagenmakers. Effects of acute (−)-hydroxycitrate supplementation on substrate metabolism at rest and during exercise in humans. Am J Clin Nutr 72; 1445-50.

Weisburger, J. H. (1999) Tea and health: the underlying mechanisms. Proc. Soc. Exp. Biol Med., 220, 271-275

Wild S, Roglic G, Green A, Sicree R, King H. (2004) Global prevalence of diabetes: estimates for the year 2000 and projections for 2030. Diabetes Care. 27:1047-1053

We claim:

1. An herbal composition comprising *Garcinia* extract, green tea extract, green coffee extract and banaba extract.

2. The herbal composition of claim 1, wherein the *Garcinia* extract is a complex metal salt of (−)hydroxycitric acid.

3. The herbal composition of claim 1, wherein the green tea extract comprises catechin polyphenols, caffeine, and L-theanine.

4. The herbal composition of claim 1, wherein the green coffee extract comprises chlorogenic acids, caffeine and polyphenols.

5. The herbal composition of claim 1, wherein the banaba extract comprises corosolic acid.

6. The herbal composition of claim 2, wherein the complex metal salt of *Garcinia* contains greater than 60% (−)hydroxycitric acid.

7. The herbal composition of claim 2, wherein the complex metal salt of *Garcinia* comprises one or more salts of (−) hydroxycitric acid in which at least one of the salts is selected from calcium, magnesium, potassium and zinc salts.

8. The herbal composition of claim 7, wherein the complex metal salt comprises calcium and the content of calcium is 20 to 80 mg per gram of complex metal salt.

9. The herbal composition of claim 7, wherein the complex metal salt comprises magnesium and the content of magnesium is 60 to 100 mg per gram of complex metal salt.

10. The herbal composition of claim 7, wherein the complex metal salt comprises potassium and the content of potassium is 20 to 100 mg per gram of complex metal salt.

11. The herbal composition of claim 7, wherein the complex metal salt comprises zinc and the content of zinc is 2 to 6 mg per gram of complex metal salt.

12. The herbal composition of claim 1, wherein a daily adult dose of the composition comprises 1950 mg to 4875 mg of *Garcinia* extract.

13. The herbal composition of claim 1, wherein a daily adult dose of the composition comprises 225 mg to 600 mg of green tea extract.

14. The herbal composition of claim 1, wherein a daily adult dose of the composition comprises 345 mg to 865 mg of green coffee extract.

15. The herbal composition of claim 1, wherein a daily adult dose of the herbal composition comprises 75 mg to 190 mg of banaba extract.

16. The herbal composition of claim 1, wherein a daily dose of the herbal composition comprises about 3900 mg *Garcinia* extract, about 450 mg green coffee extract, about 600 mg green tea extract, and about 150 mg of banaba extract.

17. The herbal composition of claim 1, wherein the composition is in an orally administered form.

18. The herbal composition of claim 17, wherein the orally administered form comprises 975 mg of *Garcinia* extract.

19. The herbal composition of claim 17, wherein the orally administered form comprises 150 mg of green tea extract.

20. The herbal composition of claim 17, wherein the orally administered form comprises 112 mg of green coffee extract.

21. The herbal composition of claim 17, wherein the orally administered form comprises 37 mg of banaba extract.

22. The herbal composition of claim 17, wherein the orally administered form is selected from the group consisting of a pill, a tablet, and a capsule.

23. The herbal composition of claim 21, further comprising an excipient.

24. The herbal composition of claim 23, wherein the excipient is selected from the group consisting of a starch, pre-gelatinized starch, dicalcium phosphate, polyvinyl povidine, magnesium stearate, talc, isopropyl alcohol, carboxymethyl cellulose, hydroxymethylcellulose, ethyl cellulose or other cellulose materials or a mixture thereof, isopropyl alcohol, and mixtures thereof.

25. The herbal composition of claim 1, further comprising a preservative.

26. The herbal composition of claim 25, wherein the preservative is selected from the group consisting of propylparaben, methylparaben, 2-bromo-2-nitropropane-1,3-diol, salts thereof, and mixtures thereof.

27. A method for reducing body weight in a mammal comprising orally administering to a mammal an effective amount of a composition comprising *Garcinia* extract, green tea extract, green coffee extract and banaba extract.

28. The method of claim 27, wherein the *Garcinia* extract is a complex metal salt of (−)hydroxycitric acid.

29. The method of claim 27, wherein the green tea extract is a full spectrum extract containing catechin polyphenols, caffeine, and L-theanine.

30. The method of claim 27, wherein the green coffee extract is a spectrum extract containing chlorogenic acids, caffeine and polyphenol.

31. The method of claim 27, wherein the banaba extract contains corosolic acid.

32. The method of claim 27, wherein the herbal composition is in an orally administered form.

33. The method of claim 32, wherein the orally administered form is selected from the group consisting of a pill, a tablet, or a capsule.

34. The method of claim 32, wherein the orally administered form further comprises an excipient.

35. The method of claim 34, wherein the excipient is selected from the group consisting of a starch, pre-gelatinized starch, dicalcium phosphate, polyvinyl povidine, magnesium stearate, talc, isopropyl alcohol, carboxymethyl cellulose, hydroxymethylcellulose, ethyl cellulose or other cellulose materials or a mixture thereof, isopropyl alcohol and mixtures thereof.

36. The method of claim 32, wherein the herbal composition further comprises a preservative.

37. The method of claim 36, wherein the preservative is selected from the group consisting of propyl paraben sodium, methyl paraben sodium, bronopol, and mixtures thereof.

38. The method of claim 32, wherein the orally administered form comprises 975 mg of *Garcinia* extract.

39. The method of claim 32, wherein the orally administered form comprises 150 mg of green tea extract.

40. The method of in claim 32, wherein the orally administered form comprises 112 mg of green coffee extract.

41. The method of claim 32, wherein the orally administered form comprises 37 mg of banaba extract.

42. The method of claim 27, wherein the herbal composition is administered between 30 and 60 minutes before a meal.

43. The method of claim 27, wherein the herbal composition is administered between 2 hours and 30 minutes before one or more meals within a day.

44. The method of claims 27, wherein the herbal composition comprises about 3900 mg *Garcinia* extract, about 450 mg green coffee extract, about 690 mg green tea extract, and about 150 mg of banaba extract.

* * * * *